United States Patent [19]

Johnson et al.

[11] Patent Number: 5,179,196

[45] Date of Patent: Jan. 12, 1993

[54] PURIFICATION OF PROTEINS EMPLOYING CTAP-III FUSIONS

[75] Inventors: Paul H. Johnson, Menlo Park; Ping Sze; Richard C. Winant, both of Palo Alto; Jerome B. Lazar, Sunnyvale, all of Calif.

[73] Assignee: SRI International, Menlo Park, Calif.

[21] Appl. No.: 347,371

[22] Filed: May 4, 1989

[51] Int. Cl.$^5$ .................. C07K 3/22; C07K 13/00
[52] U.S. Cl. .................. 530/350; 530/412; 530/415; 530/416; 530/417; 435/69.7
[58] Field of Search .............. 530/350, 412, 416, 415, 530/417; 435/69.7

[56] References Cited

U.S. PATENT DOCUMENTS

| | | | |
|---|---|---|---|
| 3,432,596 | 3/1969 | Markwardt | 424/95 |
| 4,668,662 | 5/1987 | Tripier | 514/12 |
| 4,745,177 | 5/1989 | Fritz et al. | 530/324 |
| 4,767,742 | 8/1988 | Dodt et al. | 514/12 |
| 4,897,348 | 1/1990 | Johnson et al. | 435/69.1 |

FOREIGN PATENT DOCUMENTS

| | | |
|---|---|---|
| 0114506 | 8/1984 | European Pat. Off. |
| 0158564 | 10/1985 | European Pat. Off. |
| 0252854 | 1/1986 | European Pat. Off. |
| 0207044 | 12/1986 | European Pat. Off. |
| 0211299 | 2/1987 | European Pat. Off. |
| 0212960 | 3/1987 | European Pat. Off. |
| 0225633 | 6/1987 | European Pat. Off. |
| 0227938 | 7/1987 | European Pat. Off. |
| 0286956 | 10/1988 | European Pat. Off. |
| 2611723 | 2/1987 | France |
| 8501067 | 3/1985 | PCT Int'l Appl. |
| 8603517 | 6/1986 | PCT Int'l Appl. |

OTHER PUBLICATIONS

Pharmacia, 1980, "Ion Exchange Chromatography: Principles and Methods", Rahmr i Lund, Sweden, pp. 29-33.
Ochoa, J. L., 1978, Biochimie, 60: 1-15.
Sofer et al., 1983, Bio Technique, Nov./Dec., pp. 198-203.
Pharmaceuticals, p. 14, Mar. 1986, English Abstract (corresponding to EP 168,342).
Pharmaceuticals, pp. 5-6, week 8607, English Abstract (corresponding to EP 171,024).
Pharmaceuticals, p. 9, week 8636, English Abstract (corresponding to EP 193,175).
Pharmaceuticals, p. 6, English Abstract, (corresponding to EP 209,061).
Pharmaceuticals, p. 6, week 8646, English Abstract, (corresponding to EP 200,655).
Harvey et al., (1986), *Proc. Natl. Acad. Sci. U.S.A.* 83: 1084-1088.
Dodt et al., (1986) *FEBS* 3830 202(2): 373-377.
Fortkamp et al. (1986) *DNA* 5(6): 511-517.
Chang (1983) *FEBS* 1044 164(2): 307-313.
Baskova et al., (1983) *Thromb Res* 30: 459-467.
Markwardt (1985) *Biomed Biochim Acta* 44: 1007-1013.
Green et al., (1989) *Mol Cell Biol* 9(4): 1445-1451.
Waleh & Johnson (1985) *Proc. Natl. Acad. Sci. U.S.A.* 82: 8389-8393.

*Primary Examiner*—Charles L. Patterson, Jr.
*Assistant Examiner*—Keith C. Furman
*Attorney, Agent, or Firm*—Morrison & Foerster

[57] ABSTRACT

The present invention provides a process for the recovery of heterologous proteins from CTAP-III fusion proteins comprising expressing a fusion protein having a first amino acid sequence, a second amino acid sequence, and a selectable site which may be cleaved to provide first and second polypeptide fragments, respectively, wherein the first amino acid fragment is homologous to CTAP-III, and the first and second fragments have different pI values; cleaving the fusion protein to provide the first and second fragments; and separating the first and second fragments by ion exchange chromatography.

4 Claims, 14 Drawing Sheets

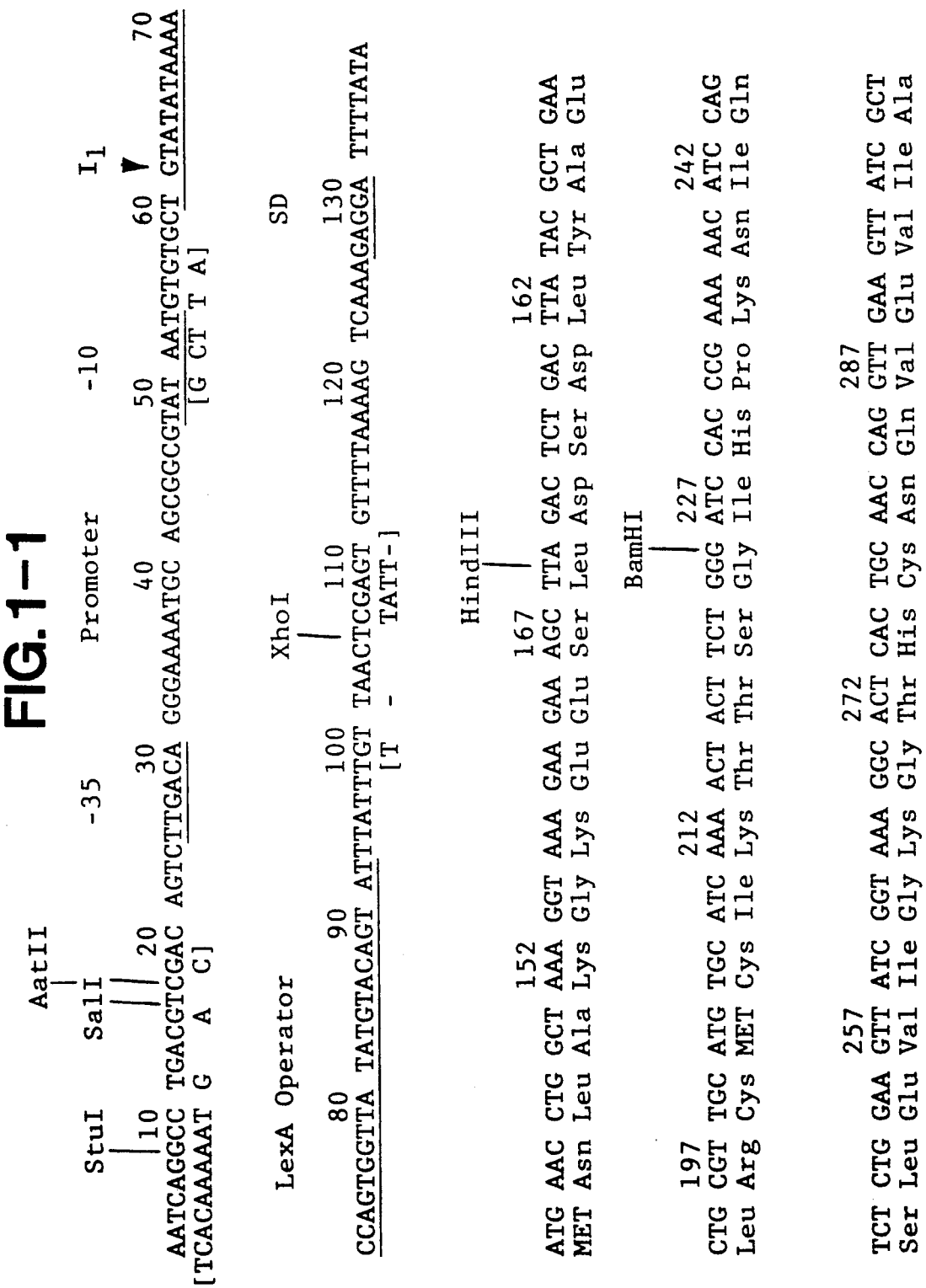

```
              (1)                              ↓
AATTCGTTAAC ATGGTTGTAT ACACTGATTG CACCGAATCT GGTCAGAACC
    GCAATTG TACCAACATA TGTGACTAAC GTGGCTTAGA CCAGTCTTGG
                           (2)                      ↑
   (3)           ↓                    (5)
 TGTGCCTGTG TGAAGGTTCC AACGTATGCG GCCAAGGTAA CAAGTGCATC
 ACACGGACAC ACTTCCAAGG TTGCATACGC CGGTTCCATT GTTCACGTAG
                 (4)          ↑                    (6)
 BamHI
   ↓             (7)
 CTGGGATCCG ACGGCGAGAA GAACCAGTGC GTAACCGGTG AAGGTACCCC
 GACCCTAGGC TGCCGCTCTT CTTGGTCACG CATTGGCCAC TTCCATGGGG
     ↑                          (8)                 ↑

(9)                         ↓
 GAAACCGCAG TCTCACAACG ACGGCGACTT CGAAGAGATC CCGGAGGAAT
 CTTTGGCGTC AGAGTGTTGC TGCCGCTGAA GCTTCTCTAG GGCCTCCTTA
         (10)                                    ↑

(11)
 ACCTGCAATA ATGACTGCAG AAGCTTG
 TGGACGTTAT TACTGACGTC TTCGAACTTAA
                 (12)
```

FIG.2

```
                          (1)
    10         20         30                    50
5'-AATTCGTTAA CATGGAAGCT GAAGAAGACG GTGACCTGCA ATGCCTGTGC
   GCAATT     GTACCTTCGA CTTCTTCTGC CACTGGACGT TACGGACACG
                          (2)

(3)
    60         70         80         90         100
GTTAAGACCA CTTCTCAGGT ACGTCCGCGT CACATCACTT CTCTGGAAGT
CAATTCTGGT GAAGAGTCCA TGCAGGCGCA GTGTAGTGAA GAGACCTTCA
                          (4)

(5)                              (7)
   110        120                   140        150
AATCAAAGCT GGTCCGCACT GTCCGACTGC TCAGCTGATC GCTACTCTGA
TTAGTTTCGA CCAGGCGTGA CAGGCTGACG AGTCGACTAG CGATGAGACT
                          (6)

XbaI       (9)
 A   160                   180        190        200
AAGACGGTCG TAAAATCTGT CTAGACCTGC AAGCTCCACT GTACAAGAAG
TTCTGCCAGC ATTTTAGACA GATCTGGACG TTCGAGGTGA CATGTTCTTC
 T         (8)                                  (10)

(11)
              220        230        240
ATCATCAAAA AACTGCTGGA ATCTTAATGA CTGCAGAAGC TTG
TAGTAGTTTT TTGACGACCT TAGAATTACT GACGTCTTCG AACTTAA-5'
                                             (12)
```

FIG.3

```
                              (1)
         10         20         30    ↓              50
5'-AATTCGTTAA CATGGAAGCT GAAGAAGACG GTGACCTGCA ATGCCTGTGC
       GCAATT GTACCTTCGA CTTCTTCTGC CACTGGACGT TACGGACACG
                              (2)                      ↑

(3)
         60         70         80    ↓    90        100
   GTTAAGACCA CTTCTCAGGT ACGTCCGCGT CACATCACTT CTCTGGAAGT
   CAATTCTGGT GAAGAGTCCA TGCAGGCGCA GTGTAGTGAA GAGACCTTCA
                              (4)                    ↑

(5)                              (7)
        110        120         ↓        140        150
   AATCAAAGCT GGTCCGCACT GTCCGACTGC TCAGCTGATC GCTACTCTGA
   TTAGTTTCGA CCAGGCGTGA CAGGCTGACG AGTCGACTAG CGATGAGACT
                              (6)          ↑

XbaI           (9)
        160        170  ▽    180        190        200
   AAAACGGTCG TAAAATCTGT CTAGACCTGC AAGCTCTGCT GTACAAGAAG
   TTTTGCCAGC ATTTTAGACA GATCTGGACG TTCGAGACGA CATGTTCTTC
                (8)            Δ                   (10)

(11)
       ↓           220        230        240
   ATCATCAAAG AACACCTGGA ATCTTAATGA CTGCAGAAGC TTG
   TAGTAGTTTC TTGTGGACCT TAGAATTACT GACGTCTTCG AACTTAA-5'
                   ↑            (12)
```

FIG.4

```
ATG GAA ACC GCG GTA ATG AAC CTG GCT AAA GGT AAA GAA AGC TTG GAC TCT
MET Glu Thr Ala Val MET Asn Leu Ala Lys Gly Lys Glu Ser Leu Asp Ser

GAC TTA TAC GCT GAG CTC CGT TGC CTG ATC AAA ACT ACT TCT GGG ATC CAC
Asp Leu Tyr Ala Glu Leu Arg Cys Leu Ile Lys Thr Thr Ser Gly Ile His

CCG AAA AAC ATC CAG TCT CTG GAA GTT ATC GGT AAA GGC ACT CAC TGC AAC CAG
Pro Lys Asn Ile Gln Ser Leu Glu Val Ile Gly Lys Gly Thr His Cys Asn Gln

GTT GAA GTT ATC GCT ACT CTG AAA AAC GGT CGT AAA ATC TGT CTA GAC CCG GAC
Val Glu Val Ile Ala Thr Leu Lys Asn Gly Arg Lys Ile Cys Leu Asp Pro Asp

GCT CCA CGT ATC AAG AAG ATC GTT CAG AAA CTG GCT GGT GAC GAA TCT GCT
Ala Pro Arg Ile Lys Lys Ile Val Gln Lys Leu Ala Gly Asp Glu Ser Ala

GAC AGA ATT CGT ATG CCG TGC GAT GGT CCG GAC TCC GGC CGT CAG TTC GCT
Asp(Arg Ile Arg)MET Pro Cys Asp Gly Pro Asp Ser Gly Arg Gln Phe Ala

CGT TCT TAC CAG GAC CCG GTT ACC CTG CAG CTG GCT AGC GTT TGC GAC CCG
Arg Ser Tyr Gln Asp Pro Val Thr Leu Gln Leu Ala Ser Val Cys Asp Pro
                                                      ↓
                                                      Cys

GGC TAC ATC GGT TCT CGT TGC GAC GAC TAA TGA .
Gly Tyr Ile Gly Ser Arg Cys Asp Asp   .
```

FIG.5

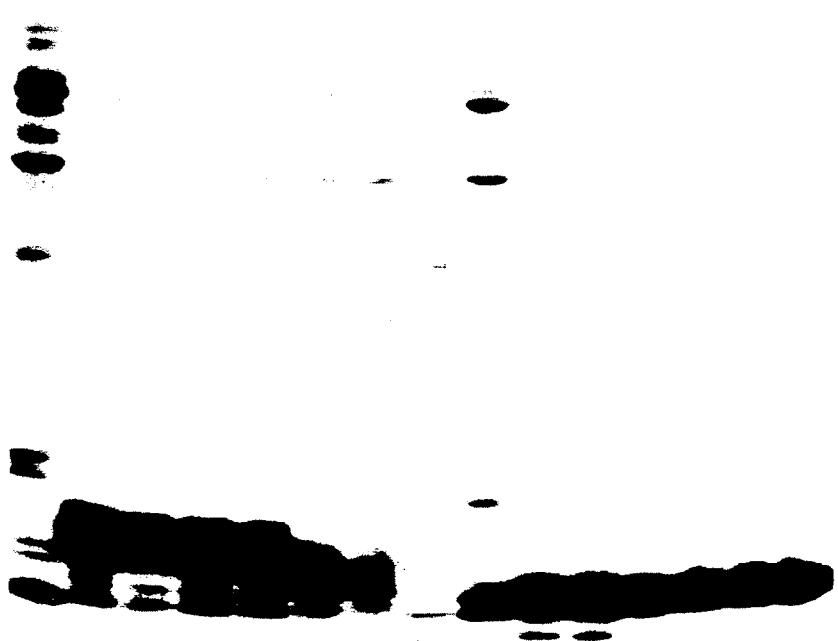

5,179,196

PURIFICATION OF PROTEINS EMPLOYING CTAP-III FUSIONS

TECHNICAL FIELD OF THE INVENTION

The present invention relates generally to the fields of biotechnology and protein purification. More particularly, the invention relates to the fields of protein expression, recombinant DNA technology to create stably expressed fusion proteins and improve the yield of poorly expressed polypeptides in microbial hosts, and the purification of the individual components of the fusion protein.

BACKGROUND OF THE INVENTION

Many heterologous proteins are not capable of being expressed in *Escherichia coli* in any measurable yield, or even if detectable, are not capable of being expressed at such commercially recoverable levels due to instability of the foreign protein in the host. Small proteins (e.g., peptide hormones of less than 100 amino acids) appear to be especially sensitive to degradation or host proteolysis. The degree of instability varies from host to host and protein to protein.

Thus, in many situations, for reasons which have not been completely resolved, heterologous proteins, despite the use of active transcriptional promoters and high copy number plasmids, are produced in only minor amount, or not at all, in a microorganism host. Moreover, as described in greater detail herein, expression systems which are quite adequate for laboratory scale expression of a desired protein are not suitable for high-density fermentation.

One of the ways in which instability or proteolytic degradation problems have been resolved employs the use of a DNA sequence encoding an additional protein which, on its own, is stable in the host cell and joining this sequence to the coding sequence of the desired protein. A small number of prokaryotic proteins have been used as the fusion partner in this manner: *E. coli* lacZ, trpE, chloramphenicol acetyl transferase (CAT), recA and lambda cII, for example.

While the literature establishes that fusion proteins are useful to express heterologous proteins in bacteria, efforts to use mammalian proteins as the fusion partner to express or to increase the recoverable yield of heterologous proteins have not been reported. More particularly, there is no reported use of human connective tissue-activating peptide-III (also referred to herein as CTAP-III) as one component in a fused protein construct to stabilize the expression of a poorly expressed or unstable protein. In light of the fact that many important proteins cannot be successfully expressed in bacteria in any commercially recoverable yield, there is a need to develop systems suitable for high density fermentation for the bacterial expression and recovery of such proteins.

DISCLOSURE OF THE INVENTION

The invention is a method for producing a heterologous protein in a microorganism, comprising:
 (a) expressing a fusion protein having a first amino acid sequence, a second amino acid sequence, and a selectable site which may be cleaved to provide first and second polypeptide fragments, respectively, wherein said first fragment is homologous to CTAP-III, said first and second fragments having first and second pI values;
 (b) cleaving said fusion protein to provide first and second fragments; and
 (c) separating said first and second fragments by ion exchange chromatography.

In preferred embodiments of this method the first amino acid sequence encodes CTAP-III(Leu$_{21}$) and the second amino acid sequence corresponds to hirudin or a laminin B$_1$ peptide Anion exchange chromatography is employed, following cleavage of the fusion protein by cyanogen bromide to separate the polypeptides, which has been found be a particularly effective purification step for recovery of the polypeptide of interest.

BRIEF DESCRIPTION OF THE DRAWINGS

FIG. 2 is a diagram showing the ligation strategy for constructing the synthetic gene for the hirudin variant 1 (HV-1).

FIG. 3 is a diagram showing the ligation strategy for constructing the synthetic gene for platelet factor 4 (PF4).

FIG. 4 is a diagram showing the ligation strategy for constructing the synthetic gene for platelet factor 4 variant 1 (PF4var1).

FIG. 5 is a diagram showing the nucleotide and amino acid sequence of the pBR-CRM/CTAP(Leu$_{21}$)-/HIR fusion protein.

FIG. 8 is a diagram showing the instability of free hirudin and the stability of free CTAP-III expressed in *E. coli*.

MODES FOR CARRYING OUT THE INVENTION

A. Definitions

Figures 1, 2:
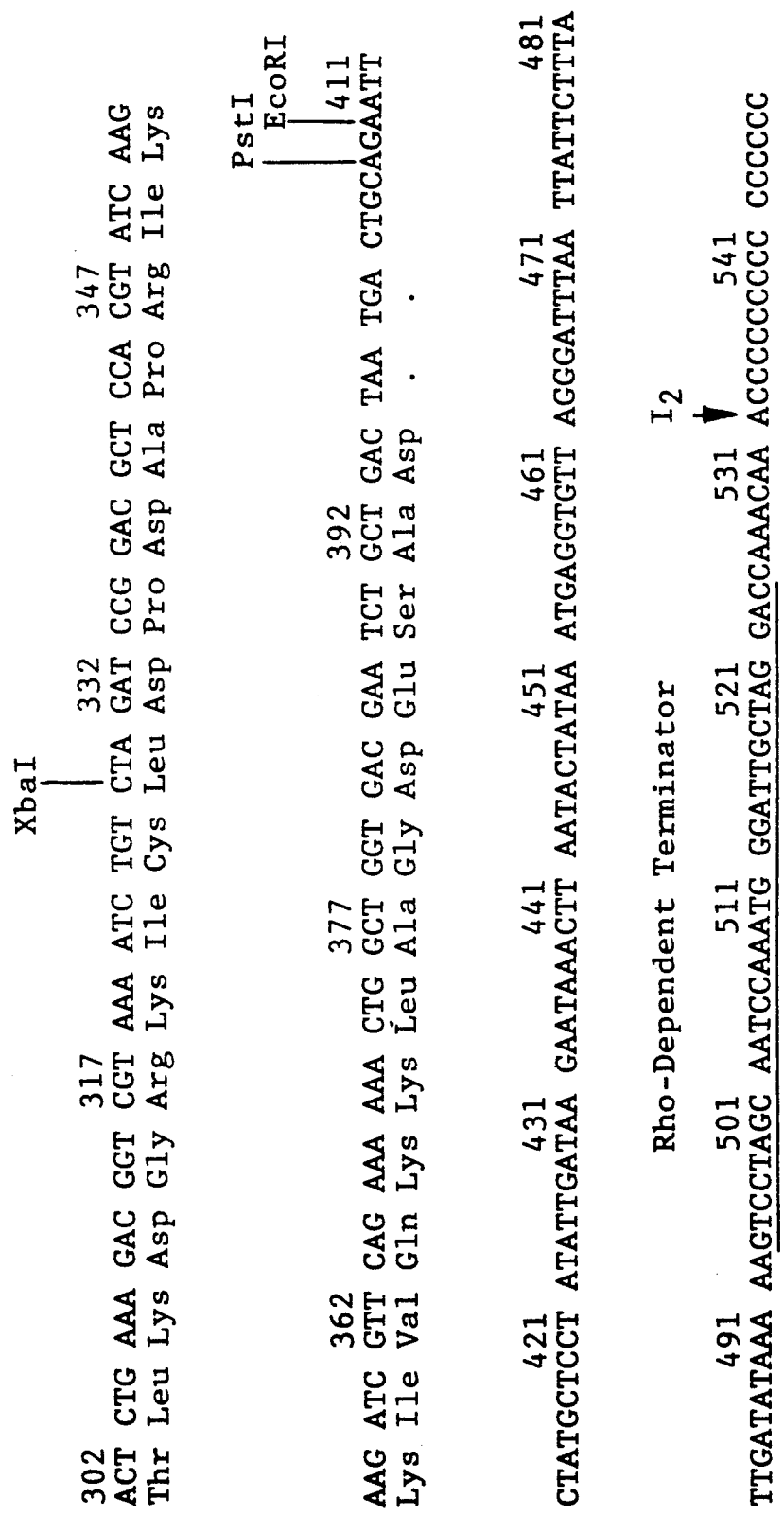
FIGS. 1-1 and 1-2 is the nucleotide sequence and major structural features of the bacterial expression system for the CTAP-III protein.

The terms "heterologous protein", "heterologous peptide", "heterologous polypeptide" are used interchangeably herein and refer to a peptide at least a portion of which is not normally contained within the genome of the host cell. Examples of heterologous proteins include viral and eukaryotic peptides encoded by cDNA, genomic DNA, or synthetic DNA, or combinations thereof.

As used herein the term "stabilizing protein expression" refers to a property of the human connective tissue-activating peptide-III component of the fusion protein that confers unusually high in vivo stability to a foreign protein. For example, hirudin has a half-life in E. coli of approximately 10 minutes, yet the CTAP-III hirudin fusion has a half-life greater than 10 hours.

"High density fermentation" refers to a level of cell density corresponding to approximately an optical density greater than 10 at 650 nm and which results in protein yields in about 50 to 1000 mg/l.

"High protein expression" or "enhanced protein expression" refers to a level of expression wherein the fused protein can comprise 5% or more of the total protein produced by each cell. A preferred range for high protein expression levels is from 10 to 30% or more of total cell protein.

"Connective tissue-activating peptide-III" or "CTAP-III" as used herein refers to a naturally occurring polypeptide isolated from human platelets that is capable of activating connective tissue cells. A synthetic gene which encodes human CTAP-III or an analog of CTAP-III in which the methionine at position 21 is replaced with leucine is described in International Publication no. WO85/01067, published Mar. 14, 1985, and is specifically incorporated herein by reference.

"Homologous CTAP-III polypeptide" as used herein refers to an amino acid composition and sequence that is (a) substantially similar to the native, human CTAP-III primary sequence, and (b) has biological activity that is common to native CTAP-III. Substantial similarity of amino acid sequence means that the sequences are identical or differ by one or more amino acid alterations (deletion, additions, substitutions) that do not cause adverse functional dissimilarities between the altered protein and native human CTAP-III.

"Differential isoelectric point" or "differential pI" as used herein contemplates a minimum threshold level difference of approximately 1.5 pH units between the CTAP-III polypeptide and the heterologous peptide of interest. This difference permits the separation of the CTAP-III molecule from the heterologous polypeptide using ion exchange chromatography under suitable pH conditions. If the heterologous protein of interest has a pI similar to that of CTAP-III(Leu$_{21}$) (which has a pI of approximately 7.8), site-directed mutagenesis techniques may be used to introduce specific cleavage sites into the CTAP-III polypeptide. The altered CTAP-III molecule will, upon cleavage, alter the pI and the charge density of the resulting CTAP-III peptide fragments to permit effective separation of the CTAP-III fragments from the heterologous protein of interest using ion exchange chromatography.

B. Human Connective Tissue-Activatinq Peptide III

CTAP-III with the leucine substitution at amino acid position 21 has been constructed using a total of 38 synthetic oligonucleotides as described in WO85/01067, supra. As shown in FIG. 1 therein, the gene is divided into three fragments: fragment I=EcoRI to BamHI; fragment II=BamHI to XbaI; and fragment III=XbaI to EcoRI. The asterisks in FIG. 1 indicate the 38 oligonucleotide boundaries. The oligonucleotides were synthesized by the phosphotriester method (Ohtsuka et al (1982) *Nuc Acids Res* 1:6553-6560), purified, characterized, and ligated to produce the full-length gene using conventional methodology.

As described in the definition section, the gene encoding CTAP-III which is used to construct the hybrid gene of the invention may include modifications of native human CTAP-III. One such modification involves replacement of the methionine at position 21 of the CTAP-III amino acid sequence (hereinafter referred to as CTAP-III(Leu$_{21}$)). The methionine may be replaced by an amino acid that does not affect the stability of the molecule adversely. Amino acids having similar hydrophobic properties and acyclic side chains such as leucine, isoleucine, and valine are preferred. Leucine is a particularly preferred replacement. The replacement of the internal methionine renders the modified protein insensitive to agents such as cyanogen bromide that cleave polypeptide chains specifically at methionine residues.

Other modifications can be made in CTAP-III to achieve the opposite effect, that is, to introduce internal methionines at positions designed to affect the isoelectric point (pI) and charge distribution of certain CTAP-III fragments which are generated upon cyanogen bromide cleavage. For proteins with a pI similar to CTAP-III(Leu$_{21}$), that is, between about 6.5 and 8.5 (CTAP-III(Leu$_{21}$) has a pI of approximately 7.8), then CTAP-III(Met$_{21}$) is used in the fusion construction. Following cyanogen bromide cleavage, two CTAP-derived fragments are produced having pIs of about 4.2 and 9.3. In this case, ion exchange chromatography may be used to achieve purification of the protein of interest by suitable manipulation of the pH of the elution buffer and salt gradient elution.

CTAP-III is produced at high levels in *E. coli* under control of a modified colicin regulatory region and has a half-life so long that it cannot be accurately measured; that is the protein appears to be infinitely stable in cells. Therefore, it was chosen for use as a fusion component to test whether it would confer this stability to other proteins. In the practice of the invention, the fusion proteins so engineered can employ CTAP-III at either the amino or carboxy terminus of the heterologous peptide. Most commonly, bacterially produced fusion proteins are constructed so that the heterologous protein of interest comprises the carboxy terminus. Such constructions allow for the simultaneous release of the fusion protein and the amino-terminal methionine following cleavage at the cleavage site. Cleavage of a protein or polypeptide is defined herein as the hydrolysis of a peptide bond in a protein or polypeptide.

In contrast to the endogenous bacterial proteins used as fusion partners, CTAP-III has desirable pharmaceutical properties. CTAPs are being investigated as pharmaceuticals for regenerating connective tissue (e.g., wound healing). (See Castor et al (1985) *Biochemistry* 24:1762-1767.) Thus, in the practice of the invention the expression of the CTAP-fusion protein permits recovery of two desirable proteins in commercially viable yields.

C. CTAP-III Fusion Vectors

The bacterial plasmid vector employed for the expression of the hybrid gene of the invention is a modification of the pNP6 vector described in Waleh and Johnson [(1985) *Proc Natl Acad Sci USA* 82:8389-8393 and WO 85/01067, supra, both of which are specifically incorporated herein by reference]. This plasmid is a pBR322 derivative wherein a subfragment of the colicin E1 operon was cloned into the PstI site of pBR322. The colicin E1 subfragment consists of a colicin E1 expression control sequence comprising a promoter, an operator site for repressor binding, a ribosome binding site, a translation start codon, part of the colicin E1 structural gene, and a transcriptional terminator. The expression control sequence contains an inducible transcriptional initiation regulatory region, wherein the promoter may be regulated by a temperature sensitive repressor, lexA, a temperature inducible repressor-inactivator, recA, or by chemical induction.

Subsequent modifications to this plasmid have removed various lengths of the colicin E1 structural gene from as little as 54 nucleotides out of a total of 1566 (giving rise to the colicin-504 fusion) to as much as 1554 nucleotides (giving rise to a 4 amino acid colicin E1 peptide) Other modifications include (1) changes in the promoter region; (2) the introduction of unique restriction sites; and (3) removal of the CAP (catabolite repressor protein) sequence.

The changes in the promoter sequence were made to construct a promoter that more closely resembles a consensus promoter sequence (Hawley and McClure (1983) *Nuc Acids Res* 11:2237–2255). These changes in the −10 region of the pNP6 regulatory region have Specific embodiments of a number of heterologous proteins for use in the present invention are discussed below.

Hirudin is a small protein isolated from the salivary glands of the medicinal leech, *Hirudo medicinalis*. It is the most potent and most specific known inhibitor of thrombin, the serine protease that functions in regulating hemostasis and that catalyzes the step in blood coagulation—the conversion of fibrinogen to clottable fibrin. Hirudin has been shown to be an effective anticoagulant and antithrombotic agent in animals and humans and may be uniquely suited to the clinical treatment of venous and arterial thrombosis—particularly as an adjunct to fibrinolytic therapy, disseminated intravascular coagulation, antithrombin-III deficiency, and perhaps some forms of metastatic cancer.

The primary structures of three hirudin variants, designated HV-1, HV-2, and HV-3, have been determined and the amino acid sequence alignment is set forth below, along with a consensus sequence. The top line is HV-1, the middle line is HV-2, the third line is HV-3, and the bottom line is the consensus sequence.

```
              10         20         30         40         50         60
    vv YTDCTESGQNLCLCEGSNVCGq GNKCILGSdGe kNQCVTGEGTPkPqSHNdGDFEEIPEE_YLQ
       |||||||||||||||||||||  ||||||| |    ||||||||||| ||| ||||||||| |||
     I TYTDCTESGQNLCLCEGSNVCGKGNKCILGSnGKgNQCVTGEGTPnPeSHNnGDFEEIPEE_YLQ
       |||||||||||||||||||||||||||||||| ||  |||||||||| |||| ||||||||  |||
     I TYTDCTESGQNLCLCEGSNVCGKGNKCILGSqGKdNQCVTGEGTPkPqSHNqGDFEp IPEd a Yd e itYTDCTESGQNLCLCEGSNVCGkGNKCILGS-Gk-NQCVTGEGTPkPqSHN-GDFEeIPEe_Ylq
``` strengthened the colicin E1 promoter. Unique XhoI and HpaI restriction sites were introduced between the lexA operator and the ribosome binding (S-D) site to allow the regulatory region and coding sequence for the amino terminal domain of the inserted gene to be more easily manipulated. Several unique restriction sites (StuI, for example), have been introduced upstream of the promoter, thus permitting the expression cassette (the genetic control regions and the synthetic gene of interest) to be readily transferable. Lastly, the CAP binding region in pNP6 has been removed, thus permitting cells containing this expression plasmid to be induced in culture media containing glucose. The nucleotide sequence and major structural features of this modified expression system for CTAP-III (pNP6-CRM/CTAP) are shown in FIG. 1. Original nucleotide sequences in the promoter region are indicated by the brackets.

D. Heterologous Protein Expression

When direct expression (e.g., expression of a DNA sequence encoding a protein free from endogenous proteins or protein fragments) results in production of a stable protein in bacteria, the protein typically contains an amino-terminal methionine, which may or may not be efficiently removed by host enzymes. Secondly, it has been found that a number of foreign proteins cannot be expressed in any significant yield in bacteria. The fusion approach has been found to be useful in protecting otherwise foreign proteins or peptide products from intracellular degradation. The present invention provides for an expression vector that produces an exceptionally stable protein for use in fusions with any of a number of heterologous proteins. This vector also offers the additional benefit that CTAP-III, a mammalian protein of interest and utility, may be expressed and recovered in conjunction with the protein of interest.

The lower case letters indicate positions of variability. For the consensus sequence, lower case indicates a common position for two of the three variants. Positions denoted by a hyphen (-) and underscore (-) indicate complete variability and deletion, respectively.

Several laboratories have constructed synthetic genes for HV-1 and have expressed biologically active hirudin. Fortkamp et al [(1986) *DNA* 5:511–517; in "Hemostasis and Animal Venoms" (Pirkle and Markland, eds.) pp. 295–306, Marcel Dekker, Basel, 1988] have fused a hirudin synthetic gene to a truncated Cl repressor gene of bacteriophage lambda to create a hybrid protein with an additional methionine at the fusion point. Although the fusion protein was inactive as a thrombin inhibitor, cyanogen bromide cleavage at the single methionine released active hirudin. Similarly, Bergmann et al [(1986) *Bio Chem Hoppe Seyler* 367:731–740] have produced HV-1 as a fusion with beta-galactosidase. Dodt et al [(1986) *FEBS Lett* 202:273–277] subsequently improved expression yields using a fusion with the alkaline phosphatase signal sequence, which permitted hirudin to be excreted into the periplasm of *E. coli* and to be recovered in native form with high biological activity. Braun et al [(1988) *Biochem* 27:6517–6522] used a different secretory system, containing the signal peptide of the major outer membrane protein of *E. coli*, OmpA, to secrete correctly processed and active HV-1.

Harvey et al [(1986) *Proc Natl Acad Sci USA* 83:1084–1088] constructed cDNA libraries from leech tissues and demonstrated multiple transcripts. Northern hybridization analysis suggested the existence of three distinct mRNA species coding for hirudin, and Southern hybridization analysis suggested the existence of several genes. A cDNA coding for the HV-2 variant has been expressed intracellularly in *E. coli* under the control of the bacteriophage lambda promoter but with poor yield (EP 158,564, published Oct. 16, 1985). HV-2 was subsequently expressed in yeast with a significantly improved yield, using a secretory system that allowed correct processing of the mature protein (Loison et al (1988) *Biotechnol* 6:72-77; French 2,611,723, published Sep. 9, 1988).

While these systems are acceptable for laboratory scale production of hirudin, as evident from the results provided in Table 1, none are viewed as acceptable for high density fermentation and production of hirudin.

TABLE 1

MICROBIAL EXPRESSION OF RECOMBINANT HIRUDINS

| Organism | Vector/ Promoter | Mode[1] | Variant | Yield (mg/l) | Sp. Act. U/mg[2] |
|---|---|---|---|---|---|
| E. coli | ptg927 lam-PL | I | HV-2 | <0.01 | — |
| E. coli | pHIR21 tac | P | HV-1 | 4 | 560 IU |
| E. coli | pMF1. lacUV5/tac | I | HV-1 | 4.8 | 8,500 |
| E. coli | pHIR20 lam-PL | I | HV-1 | 0.16 | 500 IU |
| Yeast | pTG1833 PGK | S | HV-2 | 1.6 | 13,000 AT |
| E. coli | pNP6ΔRI-CRM/HIR[4] | I | HV-1 | 10-15 | 11,300 AT |
| E. coli | pIN-III-ompA2 lpp/lac | P | HV-1 | 1[3] | — |

[1]I, intracellular; S, extracellular secretion; P, periplasmic secretion.
[2]AT-U, antithrombin units; IU, international units.
[3]Yield after purification. Braun et al (1988) Biochem 27:6517.
[4]Described in Example 4 herein.

The hirudin used in the following examples is produced from a synthetic DNA encoding the HV-1 variant. However, as used herein, "hirudin" is intended to refer to any of the three variants and obvious variations thereof. The construction of the gene encoding hirudin is provided in the examples and the DNA sequence is provided in FIG. 2.

Other proteins of interest for use in the present invention include heparin binding proteins such as platelet factor 4 and a recently discovered variant protein of platelet factor 4 (collectively referred to as "PF4"). PF4 is a platelet-secreted protein with several biological functions, including procoagulation, antiheparin, immunoregulatory, and chemotactic activities.

PF4 has been isolated from bovine, rat, and human blood and purified to homogeneity (Wu et al (1977) *Prep Biochem* 7:479; Doi et al (1987) *Mol Cellular Biol* 7:898; and Levine and Wohl (1986) *J Biol Chem* 251:324, respectively) and its amino acid sequence and physiochemical properties have been determined (see Walz et al (1977) *Throm Res* 11:893). A cDNA sequence is disclosed by Poncz et al (1987) *Blood* 69:219, which encodes a full-length leader sequence of 30 amino acids preceded by a methionine and followed by the coding region for a 70 amino acid mature protein.

The bacterial expression of PF4 is disclosed in European Patent Application No. 89.300128.9, filed Jan. 6, 1989, the disclosure of which is incorporated herein by reference. As taught therein, a synthetic gene for PF4 consists of 243 base pairs of DNA that are assembled from two major subfragments (designated I and II) composed of eight and four oligonucleotides, respectively. The 12 oligonucleotides were synthesized on an Applied Biosystems DNA Synthesizer using phosphoramidite chemistry.

The 12 synthetic oligonucleotides were purified, characterized, and ligated to produce fragments I and II as illustrated in FIG. 3. The oligonucleotides used to construct this gene introduce EcoRI restriction sites at the boundaries of this gene and thus facilitates the subcloning of this gene, as a single EcoRI fragment, into an expression vector.

Recently, a variant gene of PF4, designated "PF4var1" has been discovered. The term "PF4" as used herein is intended to refer to either of these two proteins. The cloning and expression of the gene encoding this novel protein is described in Green et al (1989) *Mol Cell Biol* 9(4):1445-1451 and in co-pending U.S. patent application Ser. No. 07/302,425, filed Jan. 26, 1989, both of which are specifically incorporated herein by reference. The cDNA sequence for PF4var1 indicates that, with respect to the mature protein, the amino acid residues which differ from PF4 are all located in the carboxy portion of the molecule, specifically at locations 58 (Pro→Leu), 66 (Lys→Glu), and 67 (Leu→His). The nature of these changes may have a significant effect on the structure and function of PF4var1. In addition to these changes in the mature protein, PF4var1 includes a three arginine insert and several other amino acid variations in the leader sequence.

As taught above for PF4, a synthetic gene encoding PF4var1 may be constructed using oligonucleotides similar to those used for PF4 but containing the appropriate base changes for amino acid positions 58, 66, and 67. FIG. 4 illustrates the synthetic DNA sequence for the expression of PF4var1. The 12 oligonucleotides used to create the entire coding sequence, bounded by two EcoRI linker sequences, are depicted by the arrows above the DNA sequence.

An antimetastatic laminin peptide has also been expressed as a CTAP-fusion protein using the vector of the present invention. This peptide shares substantial homology to the region spanning amino acid residues 897 to 936 in the human laminin B1 protein (Pikkaraimen et al (1987) *J Biol Chem* 262:10454-10462). The sequence of the peptide is Pro$_1$-Cys Pro Asp Gly Pro Asp Ser Gly Arg Gln Phe Ala Arg Ser Cys Tyr Gln Asp Pro Val Thr Leu Gln Leu Ala X Val Cys Asp Pro Gly Tyr Ile Gly Ser Arg Cys Asp Asp-Y, wherein Pro$_1$ is either Pro or des-NH$_2$Pro, X is either Cys or selected from the group consisting of neutral aliphatic amino acids, and Y is either —OH or —NH$_2$. As used herein, neutral aliphatic amino acids are defined as alanine, valine, leucine, isoleucine, serine and threonine, especially serine.

A synthetic gene encoding this 40 amino acid peptide, designated herein as LamB$_1$-40, is illustrated in Example 7. The details of its construction are provided in some detail in the following examples.

E. Host Cell Culture

Host strains used in cloning and procaryotic are widely available and include *E. coli* strains such as MC1060, DH1, RR1, C600hfl, HB101, JA221, MM294, and JM101.

The regulatory mechanism of the pNP6 expression vector and its derivatives is based on the inducibility of the colicin E1 operon of *E. coli* by chemical or physical agents that damage DNA. As is known in the art, vector systems other than the colicin E1 system are similarly controlled. Mitomycin C has been shown to be a most effective chemical inducing agent. However, the use of mitomycin C for the production of proteins having pharmaceutical applications requires the complete removal or inactivation of this chemical drug during the production and purification process, which is laborious and costly.

Ultraviolet (UV) light is equally effective in inducing the colicin E1 operon. However, a UV induction system can not be easily adapted for large-scale cultures at the industrial level. Therefore, alternative mechanisms applicable to induce the expression of heterologous genes for the industrial production of their encoded recombinant proteins is needed. A desirable system should be simple, inexpensive and its use would not require special procedures in the purification process.

Since the colicin E1 promoter is regulated by negative control (for example, a repressor protein, encoded by the lexA gene, binding to the operator), transcription initiation by means of a shift in temperature may be employed. Alternatively, or in addition to, induction may be accomplished by temperature induced activation of the recA protein which results in inactivation of the lexA repressor. Thus to meet the challenge of developing a simple, inexpensive mode of induction, a temperature sensitive host strain is employed. Such strains include DM511, DM936 and DM1187 (Mount et al, (1975) *J Bacteriol* 121:1203-1207). These strains carry a mutation in either the recA or the lexA genes that are derepressed for SOS functions and express the desired hybrid gene in the pNP6 vector at high levels when the temperature shifts from 30° C. to about 42° C. As would be appreciated by those skilled in the art, plasmids carrying the ts mutations can also be employed for purposes of the present invention.

The present mode of induction to express the desired hybrid gene at high levels may also be enhanced by the addition of nucleic acid bases or nucleosides, preferably purine bases (for example, adenine or adenosine, however the free base, thymine, also works well) to the culture medium at the time of induction to amplify the effects of the recA and lexA temperature sensitive mutations and results in even higher expression of SOS regulated functions. Improvement is at least 10% greater expression beyond that observed for the temperature sensitive inductions.

F. Purification

The transformed microorganisms are grown in a suitable growth medium, typically to an optical density (OD) of at least about 10 at 650 nm, and preferably between about 20 and 40 or greater at 650 nm. The composition of the growth medium will depend upon the particular microorganism involved and will typically contain assimilable sources of carbon and nitrogen, energy sources such as glucose, and magnesium, potassium and sodium ions, and optionally amino acids and purine and pyrimidine bases.

After the cells are harvested from the culture, they may be concentrated, if necessary, to about 0.1 to 1.0 g/ml, preferably 0.2 to 0.5 g/ml by filtration, centrifugation, or other conventional methods.

Following concentration, cell lysis is achieved by disrupting the cell membranes. Conventional cell disruption techniques such as homogenization, sonication, or pressure cycling may be used in this step of the process. Preferred methods are sonication or homogenization with a Stansted Cell Disrupter. The end point of the disruption step may be monitored by optical density, with the optical density of the suspension typically decreasing about 65% to 85%. In any event, the disruption should break substantially all of the cells so that substantially no intact cells are carried through to the first purification step. Before the disruption, the ionic strength and pH of the liquid phase of the concentrate is adjusted, if necessary, to a level that facilitates removal of *E. coli* proteins in subsequent steps, while retaining the fusion protein as an insoluble complex in the cellular debris.

The pH may be adjusted by adding suitable buffers. In most instances pH's in the range of about 7.5 to about 9.0 will be used.

Solubilization of the fusion protein is performed in a chaotropic environment using a strong denaturant such as a guanidine salt or urea, although detergents such as Triton, SDS and salts of thiocyanate ion may be employed. Typically, a range of 1 to 7M concentration is workable for guanidine salts, with 4-6M being preferred while detergents are used in the range of 1-2% of solution. The pH of the solution must also be compatible with the characteristics of the fusion protein.

Once the fusion protein is solubilized, it may then be selectably cleaved in accordance with the nature of the selectively cleavable site. One of the methods for selectable cleavage is cyanogen bromide. This technique requires the absence of an available methionine other than at the site of cleavage or the ability to selectively distinguish between the methionine to be cleaved and a methionine within the polypeptide sequence. Alternatively, a protease may be employed which recognizes and cleaves at a site identified by a particular type of amino acid. Common proteases include trypsin, chymotrypsin, pepsin, bromelain, papain, or the like. Trypsin is specific for basic amino acids and cleaves on the carboxylic side of the peptide bond for either lysine or arginine. Also, enzymes exist which cleave at specific sequences of amino acids. Bovine enterokinase cleaves to the carboxylic side of lysine or arginine that is preceded by acid residues of aspartic acid, glutamic acid, or carboxymethyl cysteine. Other enzymes which recognize and cleave specific sequences include: collagenase, factor X, thrombin and polyubiquitin processing enzyme.

If solubilized protein is to be purified by ion exchange, the solubilizing agent may be removed by dialysis or an equivalent process such as diafiltration or reverse phase LC.

The steps in the recovery process subsequent to the cleavage step are primarily designed to separate the heterologous polypeptide of interest from CTAP-III and endogenous *E. coli* proteins to provide the heterologous protein at a high level of purity (preferably at least about 85% and more preferably at least about 95%) in high density yields of at least about 50 mg/l and more preferably about 50 to 500 mg/l.

Subsequent to the cleavage step, the polypeptide components of the fusion protein may be easily isolated in substantially pure form using ion exchange chromatography. Depending upon the differential charge properties of the two polypeptide components, or whether CTAP-III is to be recovered in whole or fragmented, either cation or anion exchange chromatography may be employed.

The cleaved reaction products are subjected to ion exchange chromatography to purify the heterologous protein of interest. When the heterologous protein is acidic, anion-exchange chromatography is utilized. In this instance a strong anion exchange resin having cationic groups attached to a solid support is preferred. Polysaccharide supports are generally favored and include such commonly used ion exchange resins such as, for example, beads of dextran, agarose, or cellulose.

Those skilled in the art will recognize that the strong anion exchange resin refers to resins having cat ionic groups which maintain their positive charge throughout a relatively broad pH range. The cationic groups attached to the support may be selected from quaternary ammonium groups, such as $—CH_2CH_2N^+(CH_2CH_3)_2CH_2CH(OH)CH_3$. Examples of suitable commercially available anion exchange resins for use in the practice of the invention include QAE-Sephadex A-25, DE-52, QE-52 cellulose, Cellex QAE, Mono Q and Q-Sepharose Fast Flow.

The anion exchange resin is usually employed in the form of a packed column. The column is equilibrated using conventional techniques and the solution of the cleaved reaction products is loaded onto the column. CTAP-III($Leu_{21}$), having an alkaline pI (approximately 7.8), does not bind efficiently at pH values below approximately 6.8 and the protein of interest, having an acidic pI, does bind to the column. The protein of interest is eluted by increasing the ionic strength of the buffered solution, typically from 0 to 0.75M NaCl. The column can be regenerated by washing with solutions of NaOH and nonionic detergents to remove any residual contaminating protein or solubilizing agents and equilibrating the column.

For example, when either hirudin or the laminin $B_1$ peptide is fused to CTAP-III($Leu_{21}$), an anion exchange column (for example, either Mono-Q or Q Sepharose from Pharmacia) may be employed to separate the two proteins on the basis of differences in their isoelectric points (hirudin=3.8, laminin $B_1$ peptide=3.65, CTAP-III=7.8). In a pH 5.5 buffer, hirudin binds to the anion exchange column whereas CTAP-III does not. Elution of hirudin may be performed with a linear gradient (0 to 0.5M) of NaCl. Pooled fractions of hirudin, typically greater than 90% pure, may optionally be subjected to further purification using hydrophobic interaction chromatography (HIC), gel filtration chromatography, reverse-phase liquid chromatography (RP-LC) or combinations thereof.

The ion exchange step may also employ a cation exchange column whereby anionic groups are attached to the solid support. Suitable commercially available resins for use in this embodiment include, for example, carboxymethyl (CM) cellulose and sulfopropyl Sephadex. In this environment, CTAP-III($Leu_{21}$) is bound to the column and the protein of interest, in this example, having a more acidic pI than CTAP-III will flow-through the column and may be recovered therefrom. Elution conditions for the recovery of CTAP-III are similar to that described for the anion exchange.

Likewise, for the purification of a desired protein, for example, PF4, which has a pI value similar to that of CTAP-III (approximately 7.8), the natural sequence, CTAP-III($Met_{21}$), is used in the fusion construction. Followinq cyanogen bromide cleavage, CTAP-III(-$Met_{21}$) is cleaved into two peptides with pI values approximately 4.2 and 9.3 which can be readily separated from the PF4 protein by ion exchange chromatography as described above.

Protein samples may be reduced by incubation with a reducing agent such as dithiothreitol (DTT), beta-mercaptoethanol, glutathione, or cysteine to prevent the formation of intermolecular or intramolecular disulfide bonds during the recovery procedure before use in any of the subsequent chromatography steps.

Hydrophobic interaction chromatography employs hydrophobic supports, such as phenyl-Sepharose, phenyl-TSK HPLC or phenyl-Superose. This procedure separates proteins based on the hydrophobic properties of the protein, unlike ion exchange chromatography which separates based on charge properties of the protein. The selection of appropriate buffers and elution conditions are known to one of ordinary skill in the art.

The gel filtration chromatography may be carried out in two stages that remove both pyrogenic components and protein contaminants having molecular weights higher or lower than the desired heterologous protein. (Hirudin, as an example, has a molecular weight of about 7,000 (at low pH) and runs at 28,000 (at neutral pH) kilodaltons). Gels that are capable of fractionating the solution to permit separation of the hirudin from these contaminants are commercially available. The column will be sized to permit suitable resolution of the desired components. Since, in the process of the invention, the protein has a high level of purity (virtually always as high as 85% or more) after the ion exchange step, the usual disadvantage—e.g., the lower capacity of gel filtration as compared to ion exchange, does not pertain in this case.

While gel filtration is a preferred procedure, RP-LC such as RP-HPLC, is a viable alternative. RP-LC is capable of removing molecules from the solution that have molecular weights close to the recovered heterologous protein and can not, therefore, be removed completely by gel filtration. In addition, contaminants such as bacterial endotoxin are also removed effectively by RP-LC. However, since an organic acid such as acetic acid or trifluoroacetic acid and an organic solvent such as propanol or acetonitrile is used in the elution step, traces of these eluant systems may be found bound to the purified protein.

As soon as the protein is recovered from the chromatography step, it is refolded, which in the case of hirudin, happens readily at high concentration, but for other proteins may require treatment with a sulfhydryl compound under oxidizing conditions and lower protein concentrations. Refolding conditions may include the use of a "redox" buffer containing both reduced and oxidized forms of sulfhydryl compounds, for example, beta-mercaptoethanol, glutathione, cysteamine, or cysteine as described in U.S. Pat. No. 4,511,502.

All final protein preparations may be routinely characterized by analytical HPLC, UV spectroscopy, amino acid composition, N-terminal amino acid sequence analysis, and mass spectrometry. The final yield of the purified material is at least 40 mg/l of culture, and preferably, 50 to 100 mg/l of culture.

G. Assays for Heteroloqous Proteins

There are a number of activity assays developed to determine the quality of hirudin preparations and for use in quantitating hirudin in various biochemical and pharmacological experiments. Two of these methods have been refined herein and may be used routinely and reproducibly. The first, a chromogenic substrate assay measures the inhibition by hirudin of thrombin's ability to hydrolyze small synthetic peptide substrates. The second, a fibrin-clotting assay, measures the kinetics of clot formation, using either human plasma or purified fibrinogen as the thrombin substrate.

In the chromogenic assay, antithrombin activity is achieved by measuring the inhibition of release of p-nitroaniline from the chromogenic substrate H-D-phenylalanyl-L-pipecolyl-L-arginine-p-nitroanilide dihydrochloride (S-2238, supplied by Kabivitrum) by thrombin in the presence of hirudin. Thrombin concentration is 2 nM (typically 0.12 NIH units/ml), and hirudin can be assayed reproducibly at an approximate concentration range of 0.3 to 1 nM, using 296 uM substrate in 50 mM Tris buffer, 100 mM NaCl, pH 7.8, and 0.1% polyethylene glycol-6000 (PEG). PEG is included to inhibit binding of thrombin to the plastic surface of the microplate or cuvette; for the same reason, reaction vessels are pretreated with 1% PEG-20,000 prior to assay.

Hirudin inhibits the thrombin-mediated conversion of fibrinogen into a fibrin clot. This anticoagulation activity can be assayed by monitoring clot formation when purified human fibrinogen (10 mg/ml) is mixed with thrombin (0.06 NIH units/ml) and varying hirudin concentrations in 50 mM Tris, 100 mM NaCl, 0.225% PEG, pH 7.4. The hirudin concentration at 50% inhibition is then calculated from the titration curve.

One of the assays used to measure the immunostimulatory activity of PF4 can be studied by injecting mice intravenously with an immunosuppressive agent such as concanavalin A (Con A) together with sheep red blood cells (SRBC) and measuring the reduction in the production of antibody against SRBC using a plaque-forming assay. The suppression appears to be induced by the proliferation of T-cells of the suppressor phenotype caused by Con A. PF4 restores the immune response by inhibiting or reversing the activation of suppressor T-cells.

One of the assays used to measure the activity of the laminin B$_1$ peptide measures the binding of tumor cells containing the laminin receptor to the peptide immobilized on the surface of a culture tissue (Graf et al (1987) Cell 48:989–996). This assay is a convenient and sensitive method for routine measurement of laminin cell receptor binding and therefore a good indicator of laminin antagonist activity.

The following examples further illustrate the various embodiments of the invention. These examples are not intended to limit the invention in any manner. In these examples, all temperatures are in degrees Celsius unless otherwise indicated.

EXAMPLES

EXAMPLE 1

Preparation of pNP6 Derivative Expression vectors

The construction of pNP6, a pBR322 derivative vector comprising the colicin E1 expression control sequence, is described in WO85/01067, supra, as well as in Waleh and Johnson (1985), supra, and an E. coli strain MM294 transformed with this vector was deposited in the American Type Culture Collection under ATCC number 39418. Derivatives of this vector such as pNP6ΔRI/Col(4)/CTAP(Leu$_{21}$), referred to therein as pNP6/CTAP-III-N MOD, useful in the practice of the present invention, are also described in WO85/01067 or are provided herein. A. Plasmid pNP6RI was created to remove the EcoRI site located near the tetracycline resistance gene within the original pBR322 sequence thereby creating a unique EcoRI site within the colicin gene. Vector pNP6 was digested with EcoRI under limited reaction conditions so that linear molecules (cleaved at only one of the two sites) were produced. Linear molecules of pNP6 were purified by agarose gel electrophoresis and subsequently reacted with DNA polymerase I and all four deoxyribonucleotide triphosphates to fill in the single-stranded ends. The resulting molecules were circularized in a blunt end ligation reaction using T4 ligase and then they were used to transform E. coli 294.

For transformation into E. coli 294, an overnight culture grown in L-broth was diluted 1:100 into fresh L-broth medium and incubated with shaking at 37° C. until the OD$_{600}$ was 0.6. At this time, 35 ml of culture was centrifuged at 6,000 rpm for 10 min at 4° C., and the pellet was resuspended in 20 ml of 0.05M CaCl$_2$. The cells were incubated on ice for 15 min before they were collected by centrifugation at 4,000 rpm for 10 min. The cells were resuspended in 4 ml of 0.05M CaCl$_2$ and mixed with 200 ul of a DNA solution prepared by adding 50 ul of the annealing mixture and 150 ul 10 mM Tris-HCl (pH 7.5) containing 10 mM MgCl$_2$ and 10 mM CaCl$_2$. This mixture was incubated at 0° C. for 25 min, followed by incubation at 50° C. for 10 sec and at room temperature for 10 min. At this point, 14 ml of L-broth were added and the culture was shaken at 37° C. for 30 min. Then, 480 ul of tetracycline solution, 1.25 mg/ml, were added to the culture, and the incubation was continued for another 30 min. Aliquots of 100 ul were plated on freshly prepared agar plates containing 25 ml L-broth, 1.5% agar and 25 ug/ml tetracycline. Tetracycline resistant (Tc$^r$) transformants were further tested for sensitivity to ampicillin (Ap$^s$) by plating on agar containing 25 ug/ml ampicillin.

The Tc$^r$ Ap$^s$ transformant colonies were then screened for the spontaneous production of colicin. Single colonies were spotted on L-agar plates and were incubated at 37° C. overnight. The colonies were killed by exposing them to chloroform vapor, then overlayed with 5 ml L-broth containing 0.7% agar and 0.1 ml of an overnight culture of E. coli K-12. After the agar was allowed to harden, the plates were incubated at 37° C. overnight. Colonies with a zone of inhibition around them were scored as colicin producers.

Colicin-producing transformants were selected and plasmid DNA was isolated from individual clones and digested with EcoRI to identify those that contained a single, intact EcoRI site within the colicin gene. The location of the single EcoRI site was confirmed by additional restriction endonuclease mapping.

B. Plasmid pNP6ΔRI/Col(4)/CTAP(Leu$_{21}$) was constructed by digesting pNP6ΔRI with SstII (SacII) and EcoRI restriction enzymes. The larger fragment, containing the replication- and colicin gene-regulation sequences, was separated from the smaller fragment, containing the colicin gene, by gel electrophoresis and ligated to a synthetic DNA (containing the CTAP-III(-Leu$_{21}$) coding sequence) with an SstII cohesive end at the amino-terminal coding end and an EcoRI cohesive end at the carboxy-terminal coding end, as shown below

```
——ATG GAA ACC GC    G ATG——              ——TAA TGA CTGCAG    AATTC——
   Met Glu Thr Ala   Met  CTAP-III(Leu21)
——TAC CTT TGG       CGC TAC——             ——ATT ACT GACGTCTTAA    G——
```

The resulting recombinant plasmid DNA was used to transform E. coli 294 cells; colonies selected for tetracycline resistance were tested for CTAP-III protein expression; DNA was isolated from clones demonstrating positive expression and the correct structure of the construct was verified by DNA sequence analysis. Details of the methods used are described in subsequent examples.

C. A colicin fusion vector, pNP6ΔRI/Col(150), can be prepared for design of a medium-sized hybrid gene containing 150 amino acids of colicin preceding the gene of interest. The construction of pNP6ΔRI/-Col(150)/PF4 is described in detail in European Patent Application No. 89300128.9, supra and incorporated herein by reference. Briefly, the construction of this plasmid was initiated by cloning the synthetic gene sequence encoding PF4 (illustrated in FIG. 3) into the single EcoRI site of pNP6ΔRI. This recombinant plasmid encodes a 504 amino acid colicin protein fused through a methionine residue to the 70 amino acid PF4 protein.

An improved derivative of pNP6ΔRI/Col(504)/PF4 was constructed by subsequently reducing the size of the colicin segment. Thus, a medium-sized hybrid gene was constructed by deleting approximately 1,000 bp of DNA from pNP6ΔRI/Col(504)/PF4 under partial EcoRV digestion conditions. There are three EcoRV restriction sites in pNP6ΔRI; two are within the colicin E1 structural gene and the other is within the tetracycline gene. Since transformants are selected for $Tc^r$, only the desired transformants having the EcoRV fragment deleted from the colicin gene will result. The resulting plasmid, pNP6ΔRI/Col(150)/PF4, codes for only 150 amino acids of colicin preceding the start PF4 coding sequence (at the EcoRI site), and contains a single methionine residue joining the colicin segment and PF4. The fusion of this smaller colicin segment to the PF4 protein was found to enhance the recovery and purification of PF4.

The size of the colicin fusion peptide may be reduced further to a 57 amino acid segment by deleting the region between the SstII and the single EcoRV restriction site in plasmid pNP6ΔRI/Col(150)/PF4. Purified pNP6ΔRI/Col(150)/PF4 DNA was cleaved to linear molecules with SstII restriction enzyme and then treated with T4 DNA polymerase and dCTP, conditions under which the 3' and 5' exonuclease activity of the polymerase converted the SstII-generated ends of the plasmid DNA to blunt ends. The product DNA of this reaction was cleaved with EcoRV restriction enzyme and the resulting large DNA fragment was purified, converted to circular DNA in a DNA ligase reaction and then used to transform cells. The resulting plasmid, designated pNP6ΔRI/Col(57)/PF4, codes for 57 amino acids of colicin preceding the PF4 coding sequence, and contains a single methionine residue joining the colicin segment and PF4.

These modified colicin fusion vectors were subsequently used in experiments to express both hirudin and a laminin $B_1$ peptide as described herein.

EXAMPLE 2

Construction of pBR-CRM/CTAP(Leu$_{21}$)

A. Construction of a Modified Colicin Regulatory (Promoter) Region (CRM)

A modified regulatory region of the promoter of colicin E1 was designed and constructed. The nucleotide changes introduced are summarized in FIG. 1. The synthetic 151 base-long oligomer was synthesized on an Applied Biosystems 380A DNA synthesizer, as eight fragments, four segments complementary to the other four, designed such that they share 7 to 10 base pair complementary sequences at their overlapping ends.

The synthesized fragments were purified by gel electrophoresis. The 5'-ends of the polynucleotides were phosphorylated using T4 polynucleotide kinase and labeled with [gamma-$^{32}$P]-ATP. The complementary strands were annealed and ligated.

The 151-base-pair DNA was gel purified and ligated to the EcoRI-HindIII cleaved, purified large fragment of the bacterial plasmid pBR322, thus replacing the excised Tet promoter sequence. The resulting construct was designated pBRG8. Since the synthetic promoter replaced the excised Tet promoter sequence, ampicillin resistant transformants were screened for tetracycline resistance following Mitomycin C treatment (induction of the colicin promoter) Plasmid DNA from selected colonies was purified and analyzed by restriction enzyme digestion as well as by blot hybridization for the presence of the synthetic DNA sequences. The synthetic promoter sequence was verified by double stranded DNA sequencing which is as follows:

```
5'-AATTCAGGCC TGACGTCGAC AGTCTTGACA GGGAAAATGC AGCGGCGTAT
   3'-GTCCGG ACTGCAGCTG TCAGAACTGT CCCTTTTACG TCGCCGCATA

AATGTGTGCT GTATATAAAA CCAGTGGTTA TATGTACAGT ATTTATTTGT
TTACACACGA CATATATTTT GGTCACCAAT ATACATGTCA TAAATAAACA

TAACTCGAGT GTTTTAAAAG TCAAAGAGGA TTTTATAATG GAAACCGCGG
ATTGAGCTCA CAAAATTTTC AGTTTCTCCT AAAATATTAC CTTTGGCGCC

A-5'
TTCGA-3'
```

B. The modified colicin regulatory region (CRM) was removed from plasmid pBRG8 by restriction enzyme digestion and cloned into the plasmid pNP6ΔRi/-Col(4)/CTAP(Leu$_{21}$), replacing the old colicin E1 regulatory region. The new construct was designated pNP6ΔRI-CRM/CTAP(Leu$_{21}$).

C. Plasmid pNP6ΔRI-CRM/CTAP(Leu$_{21}$) was digested with AatII and ScaI restriction enzymes and the fragment containing the colicin regulatory regions and the CTAP-III gene was purified. Plasmid pBR322 was digested with AatII and NruI restriction enzymes and the large fragment containing the ampicillin resistance gene and the replication origin was purified. The two fragments were ligated (ScaI and NruI produce blunt ends and thus can ligate together) to produce the new plasmid expression vector designated pBR-CRM/CTAP(Leu$_{21}$).

EXAMPLE 3

Hirudin Gene Construction

The synthetic gene for hirudin (FIG. 2) consists of 228 base pairs of DNA that are assembled from two major subfragments (designated I and II) composed of two sets of six oligonucleotides separated at the BamHI site. The 12 oligonucleotides were synthesized on an Applied Biosystems DNA Synthesizer using phosphoramidite chemistry.

The 12 synthetic oligonucleotides were purified, characterized, and ligated to produce fragments I and II as described below and as illustrated in FIG. 2.

Oligonucleotide Purification and Characterization

1. Purification

Polyacrylamide gels (12%) were prepared with 7M urea, 90 mM Tris-borate, and 2 mM EDTA buffer. Sample wells were formed with a comb having teeth at least 2 cm wide. After standing for 3 hours, the gel was pre-electrophoresed for ~30 minutes. Equal volumes of 1 to 5 $A_{260}$ units of the unpurified oligonucleotide sample and 7M of urea were mixed in 10 mM Tris-HCl buffer, pH. 7.5. The DNA sample was added to the gel, and a dye mixture (0.17% Bromphenol blue, 0.27% xylene cyanol, 10 mM Tris-HCl, pH 7.5) was added to one of the wells to monitor the migration rate of the oligonucleotides. Electrophoresis was performed at 400 to 600 volts until the Bromphenol blue migrated ~30 cm from the top of the gel. Both plates were removed, the gel was wrapped in plastic wrap, and the DNA was visualized using shortwave UV light. The desired band was carefully cut out using a razor blade. The piece of gel was placed in an Eppendorf tube and crushed with a glass bar. Then, 0.5 ml of TE (10 mM Tris-HCl, 1 mM EDTA, pH 7.5) was added to the tube, which was rotated overnight for DNA extraction. The tube was centrifuged at 15,000 rpm for 10 minutes, and the supernatant was recovered. The DNA sample was diluted 10 times with TE and was added to a C-18 Sep-Pak column and washed with 20 ml H$_2$O for desalting. Recovery of DNA by acetonitrile elution was generally between 50 and 80%. The eluate was lyophilized and then resuspended in 0.5 ml H$_2$O.

2. End-Labeling, Gel Electrophoresis, and Autoradioqraphy

Ten pmole of the sample was lyophilized. The dried sample was dissolved in 1 ul of 10× concentrated kinase buffer (700 mM Tris-HCl, pH 7.6, 100 mM MgCl$_2$, 1 mM KCl, 50 mM dithiothreitol), 5 ul H$_2$O, 66 pmole cold ATP, 0.6 pmole [gamma$^{32}$-P]-ATP, 1 ul spermidine (1 mM), and 1 ul T4 kinase solution containing at least 70 cohesive-end-units (NEB) of activity. The sample was incubated for 30 minutes at 37° C. After the addition of 5 ul of the dye mixture, the sample was added to a polyacrylamide gel (20%, 0.4 mm thick, 15 cm long), electrophoresed until the Bromphenol blue migrated to the bottom of the gel, and autoradiographed by exposing the gel to X-ray film for 10 to 30 minutes.

3. Annealing and Ligation of Oligonucleotides

FIG. 2 shows the 12 oligonucleotide used to construct the synthetic gene. Oligonucleotides 1 through 6 and 7 through 12 composed Fragments I and II, respectively. These two fragments were assembled in vitro and sub-cloned into M13 vectors as described below.

Two sets of six purified oligonucleotides were annealed, ligated and sub-cloned into M13 vectors designated M13-HIR(I) and M13-HIR(II). For each fragment (I or II), complementary pairs of 5' end phosphorylated oligonucleotides were mixed, heated to 95° C. for 2 min, then annealed by gradual cooling to 40° C. The three double stranded oligonucleotides (with overlapping ends) for each fragment were mixed and incubated together at 37° C. for 1 h prior to ligation.

Reaction mixtures for ligation consisted of 50 mM Tris-HCl (pH 7.5), 10 mM MgCl$_2$, 20 mM dithiothreitol, 1 mM ATP, 100 pmole DNA (concentrations of 5' ends), and 100 cohesive-end-units (NEB) of T4 ligase in a total volume of 100 ul. The reaction mixtures were incubated overnight at 16° C.

4. Transformation System

E. coli was cultured in 2× YT broth until the OD$_{660}$ was between 0.6 and 0.7. Cells were collected by centrifugation, resuspended in 50 mM CaCl$_2$ (half of the culture volume), and kept on ice for 20 minutes. Competent cells were collected and resuspended in 1/10 volumes of 50 mM CaCl$_2$.

Commercially available M13 replicative form (RF) DNA, which had been previously digested with endonucleases EcoRI and BamHI, was ligated with the hirudin fragments I or II and was mixed with competent JM101 cells and kept on ice for 40 minutes. The mixture was heat-shocked at 42° C. for 2 minutes and mixed with IPTG, Bluo-gal, soft agar (46° C.), and fresh growing JM101 cells. The mixture was plated on YT agar plates and incubated overnight at 37° C.

The JM101 cells that were transformed by intact M13 synthesized beta-galactosidase and produced blue plaques. Cells that were transformed by M13 containing a hirudin fragment did not make beta-galactosidase and produced white plaques.

5. Preparation of M13 Replicative Form (RF) DNA or Plasmid DNA

One liter of cells containing the hirudin fragment were grown overnight in the presence of 25 ug/ml tetracycline and 100 ug/ml chloramphenicol (for plasmid amplification) was added at the appropriate cell density and allowed to grow overnight. The cells were harvested by centrifugation for 20 min at 5000×g at 4° C., and then suspended in 200 ml of TEN (10, 1, 150) and recentrifuged. The cells were resuspended in 5 ml of 50 mM glucose, 10 mM EDTA, and 25 mM Tris (pH 8.0) and transferred to two 30 ml screw-capped centrifuge tubes.

5 ml (2.5 ml to each tube) of 4 mg/ml lysozyme in the above buffer were added and the tubes were gently mixed by inversion and incubated for 10 min at room temperature or 30 min on ice. Next, 20 ml (10 ml to each tube) of 0.2N NaOH and 1% SDS were added to each tube. The solution was mixed gently by inversion (20 to 30 times) or by gentle vortexing and then incubated for 10 min at room temperature. About 15 ml (7.5 ml to each tube) of 3M potassium acetate and 4.4% formic acid (pH 4.8) were then added and mixed gently to allow viscous chromosomal DNA and protein to form a clot. The solution was incubated for 1 h on ice and then centrifuged for 20 min at 10,000×g. One volume of isopropanol was added to the supernatant solution and the solution was centrifuged for 10 min at 10,000×g. The supernatant was decanted and the pellets were washed with 10 ml of −20° C. 70% ethanol. The pellets were centrifuged for 5 min at 10,000×g, the ethanol was removed and the pellets were air dried in vacuo. Subsequently, the pellets were dissolved in 1.0 ml TE and treated with 20 ug/ml DNAse-free RNase A for 30 min at 37° C.

The reaction mixture was then extracted with chloroform:isoamyl alcohol (24:1) and applied (with 5% glycerol and 0.02% dye) to a 2.5 cm×25 cm BioGel A-50M agarose column. Pooled DNA fractions were precipitated with ethanol, extracted with phenol, reextracted with ether, reprecipitated with ethanol, washed, dried and resuspended in 1.0 ml TE.

6. Fragment Purification and Characterization

The recombinant phage were screened for the presence of the hirudin gene fragment I and II as follows. Phage culture was grown in a YT media containing JM101 host cells. The double-stranded replicative form (RF) DNA of M13-HIR(I) or M13-HIR(II) was isolated as described above. The single-stranded template DNA was isolated from the lysis supernatant by precipitation in 2.5M NaCl, 20% PEG (6000) for 30 min on ice, extracted with phenol, then precipitated with ethanol and sodium acetate. The sequence of both fragments was confirmed by M13 dideoxy sequencing. The fragments were removed from the RF DNA by restriction endonuclease digestion with EcoRI and BamHI and purified by SeaPlaque® agarose (Marine Colloids) electrophoresis in a buffer of 50 mM Tris-acetate, pH 8.2. The hirudin gene fragment, visualized by long-wave ultraviolet light after staining with ethidium bromide, was excised from the gel with a razor blade.

7. Ligation of the Hirudin Gene Fragments I and II

Gel slices containing the hirudin gene fragments were melted at 70° C. for 5–15 min and then equilibrated to 37° C. After an equal volume of ice-cold, 2× concentrated buffer containing T4 ligase was added, the ligation mixture was then incubated overnight at 20° C. The ligation was terminated by chelating the $MgCl_2$ with equal molar EDTA and inactivating the ligase at 70° C. for 15 min. The reaction mixture was digested with EcoRI to produce the monomer of the hirudin gene.

8. Transformation of the Intact Hirudin Gene

The EcoRI restriction reaction was terminated as above and ligated with the dephosphorylated M13 cloning vector previously digested with endonuclease EcoRI. The ligation mixture in the SeaPlaque® agarose was remelted and diluted by a factor of 10 to 50 into ice-cold TCM (10 mM Tris, pH 7.5, 10 mM $CaCl_2$, 10 mM $MgCl_2$) prior to transformation into the JM101 cells.

9. Screening the Clones and Sequencing

The recombinant phage were rapidly screened for the presence of the hirudin sequence as follows. The RF DNA was restricted with endonuclease EcoRI and the single-stranded phage DNA from clones yielding the correct diagnostic EcoRI restriction pattern was isolated as described above and used as the template for M13 dideoxy sequencing. This M13 construction has two EcoRI sites and was designated M13-HIR.

EXAMPLE 4

Construction of Hirudin Expression Vectors

A. Vector pNP6ΔRI/Col(4)/HIR

A synthetic linker-HL was designed to create an SstII site and delete the EcoRI site preceding the hirudin coding sequence in M13-HIR. The two single strand oligonucleotides of the linker were synthesized, purified, and annealed to form:

5'-CGACCGCGGTAATGGTTGT-3'

TGGCGCCATTACCAACATA

Both vector M13-HIR and annealed linker-HL were digested with endonuclease AccI and then ligated. JM101 cells were transformed with the ligated DNA, transformants were screened by SstII restriction analysis and single strand phage DNA was isolated and sequenced.

The HIR-HL fragment was separated from the vector RF using SstII and EcoRI digestions and purified by SeaPlaque® agarose gel electrophoresis. Following SstII and EcoRI digestions of the plasmid vector pNP6ΔRI/Col(4)/CTAP(Leu$_{21}$) and gel electrophoresis to remove the CTAP gene, the HIR-HL fragment was ligated into the SstII-EcoRI-digested plasmid DNA. The ligation mix was used to transform *E. coli* 294 RecA+competent cells and placed on ice for 40 min. The mixture was heat-shocked for 2 min at 42° C. and mixed with L-broth, incubated at 37° C. for 1 h before plating on LB agar plates containing 25 ml L-broth, 1.5% agar, 25 ug/ml tetracycline. The plates were incubated overnight at 37° C.

Tc$^r$ transformants were screened with endonuclease KpnI (unique to the hirudin gene) and the plasmid DNA sequence was confirmed by double strand dideoxy sequencing techniques. The plasmid expresses a small fusion polypeptide containing four residues of the colicin protein (Col4) linked to the hirudin protein by a methionine residue. Chemical cleavage of the Col(4)/hirudin fusion protein by cyanogen bromide releases free hirudin protein.

B. Vector pNP6ΔRI/Col(504)/HIR

The synthetic hirudin gene from M13-HIR was linked to the large colicin gene fragment (residues 1-504) to investigate the potential for improved expression and stability of hirudin. A synthetic linker-ColHL $$\begin{pmatrix} 5'\text{-CGACGAATTCTGTTAACCATGGTTGT-3'} \\ \text{TGCTTAAGACAATTGGTACCAACATA} \end{pmatrix}$$

was designed to facilitate cloning and adjust the reading frame of the hirudin gene in the new vector. The two single strand linker oligonucleotides were synthesized, purified, annealed and ligated to an AccI-digested fragment from M13-HIR RF containing the hirudin gene. The ligated DNA was transformed into JM101 cells and transformants screened by HpaI and EcoRI digestions and single strand phage DNA was sequenced.

The HIR-ColHL fragment was separated from the M13RF by EcoRI digestion, purified by SeaPlaque® agarose gel electrophoresis and then cloned into the single EcoRI site of the plasmid expression vector pNP6ΔRI. Tc$^r$ transformants were screened with endonuclease HpaI for the presence of the insert and PstI for the orientation of the insert. The plasmid DNA sequence was confirmed by double-strand dideoxy techniques. This expression vector produces a large fusion protein of hirudin including residues 1–504 of the colicin gene.

C. Vector pNP6ΔRI-CRM/HIR

A synthetic linker

was designed to create an XhoI site and eliminate the 5' EcoRI site from M13-HIR. The two single stranded oligonucleotides of the linker were synthesized, purified, annealed and ligated to a hirudin-containing AccI fragment from M13-HIR RF. The M13-HIR-link RF DNA from transformed JM101 cells was screened with XhoI and the single strand phage DNA was sequenced.

The HIR-link fragment was removed from the RF using XhoI and EcoRI digestions and separated by SeaPlaque® agarose gel electrophoresis. Then the fragment was cloned into the vector pNP6ΔRI-CRM/CTAP(Leu$_{21}$) (described in Example 2B), which had been previously digested with XhoI and EcoRI to remove the CTAP gene.

Tc$^r$ transformants were screened with endonuclease KpnI—a unique site that resides within the hirudin gene. The plasmid DNA sequence was confirmed by double-strand dideoxy techniques. This construction was designated pNP6ΔRI-CRM/HIR and contains the improved colicin regulatory region (CRM).

D. Construction of Derivative Vector for Colicin-Hirudin Fusions

The construction of the colicin-hirudin gene fusions are similar to the methodology taught in Example 1C for the derivative vectors comprising the colicin-PF4 hybrid gene sequences. The vector pNP6ΔRI/Col(150)/HIR was constructed by removing an approximately 1,000 bp EcoRV fragment from pNP6ΔRI/Col(504)/HIR vector and the pNP6ΔRI/Col(57)/HIR vector was constructed by removing an approximately 279 bp SstII-EcoRV fragment from pNP6ΔRI/Col(150)/HIR.

E. Construction of pBR-CRM/CTAP(Leu$_{21}$)/HIR

Figure 6:
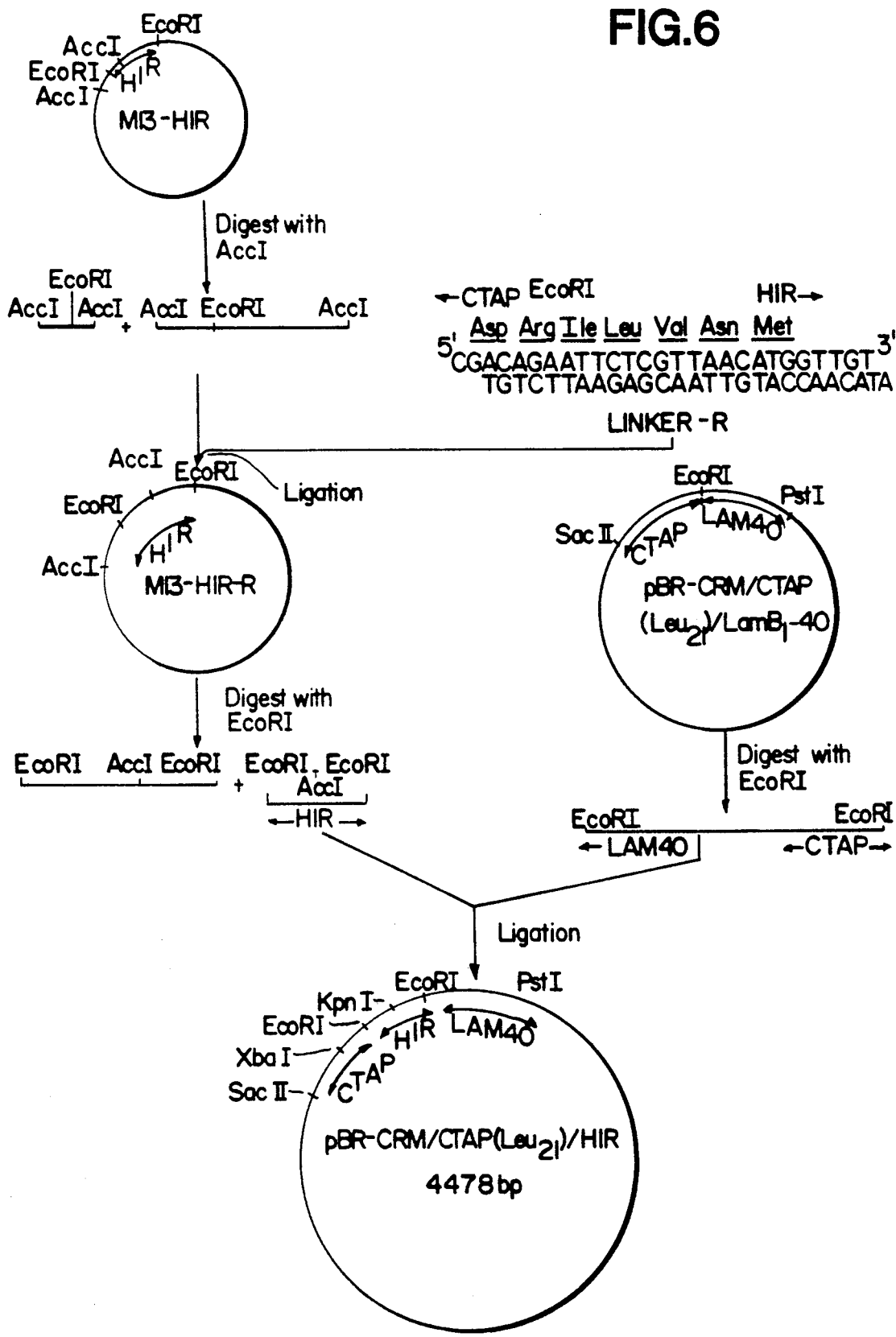
FIG. 6 is a diagram summarizing the construction the CTAP-III(Leu$_{21}$)/HIR expression vector.

The hirudin gene was inserted into the expression vector for the laminin B$_1$ peptide (described in Example 7C) as illustrated in FIG. 6. A synthetic linker-R was designed to facilitate insertion of the hirudin gene in the correct reading frame with the CTAP gene. The two single stranded oligonucleotides of the linker were synthesized, purified, annealed, and ligated to a hirudin containing AccI digestion fragment from M13-HIR RF. The ligated DNA was used to transform JM101 cells. The transformants of M13-HIR-R were screened by M13 single strand dideoxy sequencing.

The HIR-R fragment was separated from the RF by EcoRI digestion and SeaPlaque® agarose gel electrophoresis. The HIR-R fragment was inserted into the single EcoRI site of pBR-CRM/CTAP(Leu$_{21}$)/LamB$_1$-40 between the CTAP gene and the LamB$_1$-40 gene. Following cell transformation, tetracycline resistant (Tc$^r$) transformants were then screened with endonucleases KpnI, for the presence of the hirudin gene, and HpaI, for the correct orientation of the insert. The correct plasmid DNA sequence was confirmed by double strand-dideoxy sequencing techniques and the DNA for the fusion protein is shown in FIG. 5.

The resulting plasmid expression vector for hirudin, designated pBR-CRM/CTAP(Leu$_{21}$)/HIR, produces an exceptionally stable fusion protein between CTAP(-Leu$_{21}$) and hirudin, joined by a five-amino acid segment (Arg-Ile-Leu-Val-Asn) and a single Met just preceding the hirudin protein sequence.

EXAMPLE 5

Stability Study-Pulse and Chase Labeling

Typically 100 ml of E. coli RecA+ cultures containing synthetic genes from the collection of pNP6 colicin derivative plasmids encoding either free or fusion genes were grown in M9CA medium: (42 mM Na$_2$HPO$_4$, 22 mM KH$_2$PO$_4$, 8.6 mM NaCl, 1.8 mM NH$_4$Cl, 2 mM MgSO$_4$, 0.5% glucose, 0.1 mM CaCl$_2$, 1 mM thiamine-HCl, 0.2% casamino acid) at 37° C. until the OD$_{660}$=0.-36–0.4. Typically a 0.5 ml culture aliquot was labeled (t=0) with 50 uCi of [$^{35}$S]-cysteine for 15 min at 37° C. Following this 15' interval, the 100 ml culture was induced with 1 ug/ml Mitomycin C and simultaneously the 0.5 ml [$^{35}$S]-labeled cells were centrifuged, resuspended in protein gel sample buffer (1% SDS, 0.14M beta-mercaptoethanol, 20% glycerol, 40 mM Tris, pH 6.8, 0.05% bromphenol blue (BPB)), heated at 95° C. for 5 min and kept on ice as the pre-induction control. After the culture was induced for 105 min, a 5 ml aliquot was removed and labeled with 0.5 mCi of [$^{35}$S]-cysteine for 15 min at 37° C. with shaking. The cells were centrifuged, the cell pellet was washed, and then resuspended in 5 ml of M9CA medium and incubated at 37° C. A series of 0.5 ml culture samples were collected at various intervals and provided as described above. The time series samples were immediately analyzed by 15% polyacrylamide/SDS gel electrophoresis. The gel was fixed in 10% acetic acid for 10 min, rinsed, washed in water for 15 min, treated with 1M sodium salicylate for 60 min, vacuum dried at 60° C. for 2 h and autoradiographed by exposing the gel to X-ray film for 6 to 8 h.

As shown in FIG. 8, hirudin expressed in plasmid pNP6ΔRI/HIR (or pNP6-CRM/HIR), i.e., not as a fusion protein, has a half-life of approximately 10 min while CTAP-III, expressed under similar conditions, is completely stable for at least 10 h.

Figure 9:
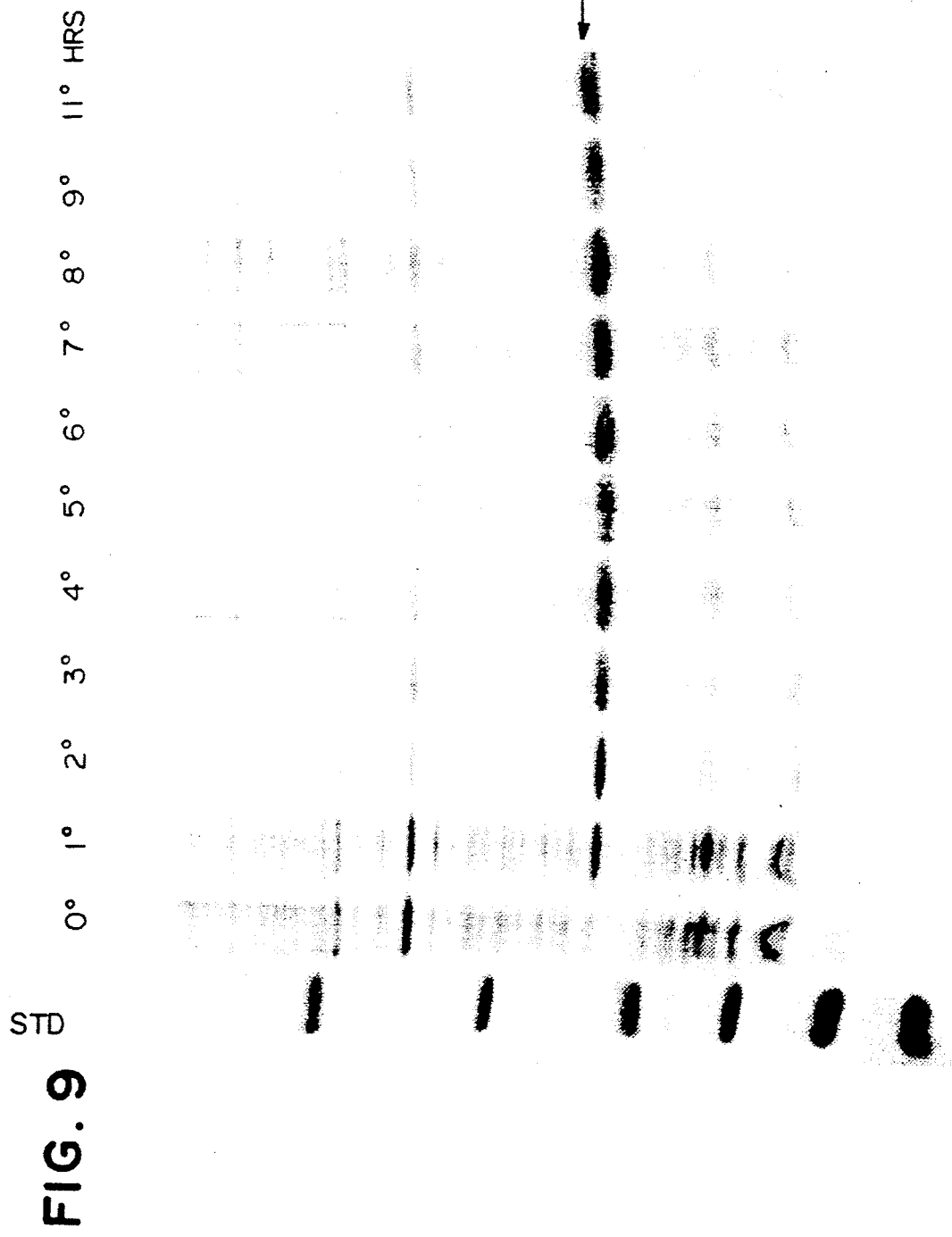
FIG. 9 is a diagram demonstrating the stability of the CTAP-III/hirudin fusion protein up to 11 hours after induction of expression in *E. coli*.

Additional pulse-chase experiments were conducted using each of the colicin-hirudin fusion vector constructions and demonstrated, for example, that the colicin-hirudin fusion proteins, e.g., Col(57)/HIR and Col(150)/HIR exhibited a half-life similar to (or less than) that observed for the direct expression of hirudin. In contrast, FIG. 9 shows the results on a polyacrylamide gel (stained with silver) which demonstrates the stability of the CTAP-III/hirudin fusion protein 11 h after induction of expression in E. coli transformed with vector pBR-CRM/CTAP(Leu$_{21}$)/HIR.

EXAMPLE 6

Purification of Recombinant Hirudin (HV-1)

Figure 10:
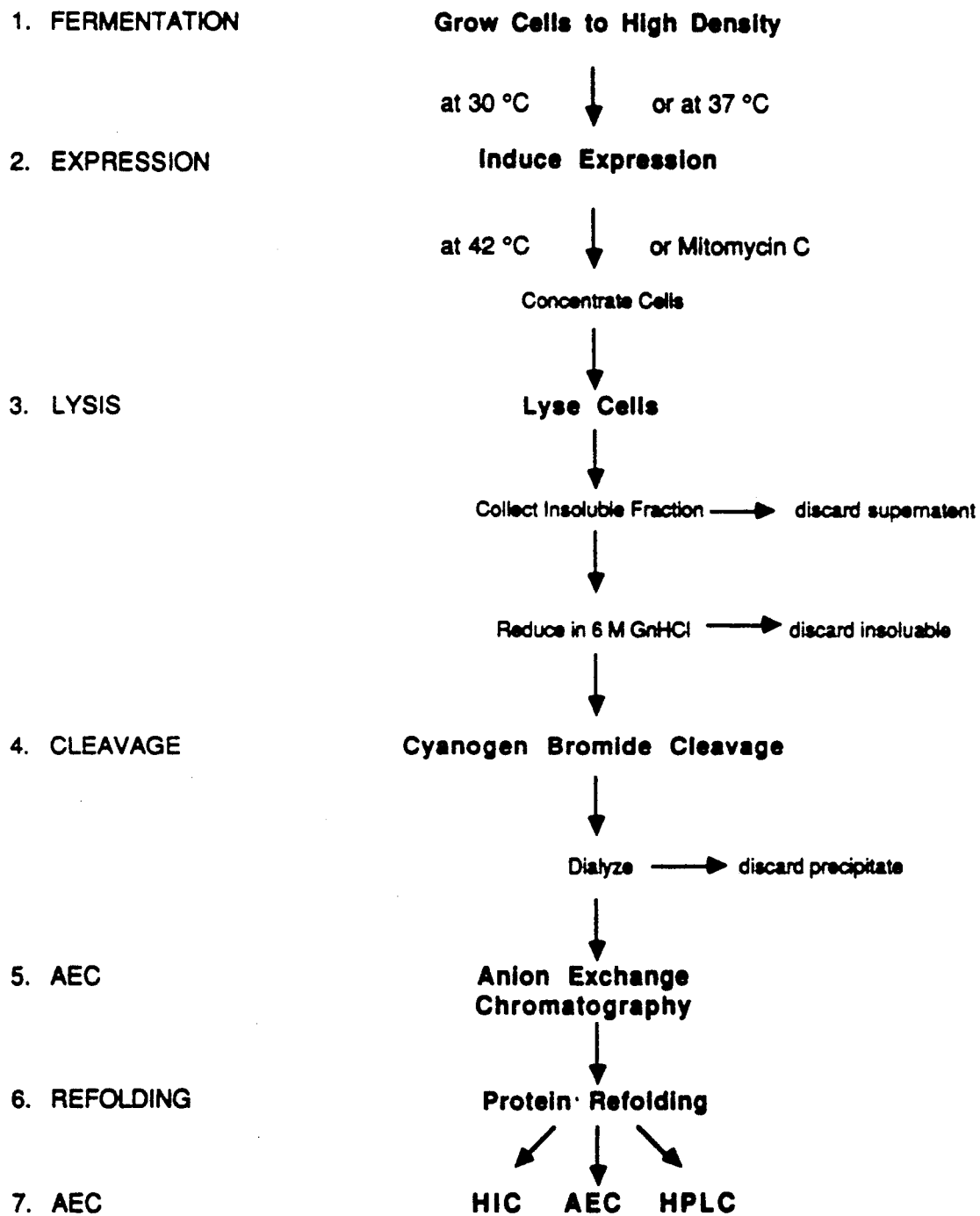
FIG. 10 is a flow diagram illustrating the purification procedure for hirudin.

FIG. 10 provides a flow diagram illustrating the purification procedure described below for recombinant hirudin:

A. Fermentation

One ml frozen culture of E. coli strain 294 (pBR-CRM/CTAP(Leu$_{21}$)/HIR), stored at −80° C. in 15% glycerol, was thawed and used to inoculate 500 ml of L-broth (10 g tryptone, 5 g yeast extract, 10 g NaCl per liter) containing tetracycline at a final concentration of 20 ug/ml. The pH of the broth was adjusted to 7.0 with 1N NaOH. The culture was then incubated overnight in a shaking 37° C. incubator. The following day, this culture was used to inoculate either 2 liters of L-broth prepared in a 6-liter flask, or 10 liters of fermentation medium in a 16-liter vessel. The size of the inoculum is about 2% of the total volume of the medium.

E. coli cells containing the expression plasmid for hirudin (pBR-CRM/CTAP(Leu$_{21}$)/HIR were grown in minimal media at either 37° C. or at 30° C. (the latter temperature for strains carrying a lexA or a recA temperature sensitive (ts) mutation) to a cell density corresponding to an optical density at 650 nm of 4 (laboratory scale) or 30 (high density fermentation scale). [Minimal medium comprises (given in quantities or volumes per liter) 7.1 g (NH$_4$)$_2$SO$_4$, 1.7 g K$_2$PO$_4$, 1.5 g sodium citrate, 5 g casamino acids supplemented with 100 ml 20% glucose, 8.3 ml 1M MgSO$_4$, 1.7 ml 1M CaCl$_2$, 1.8 ml 0.1M FeCl$_3$, 0.2 ml trace elements, 10 ml vitamins.] The cells are then induced by adding Mitomycin C to a final concentration of 1 ug/ml, or by increasing the temperature to 42° C. (for 20 min) followed by adjustment to 37° C., and the cells were allowed to grow for an additional 4 hours. Oxygen levels were maintained between 40 and 60% saturation, the pH of the culture medium was maintained at pH 7-7.5 by the addition of ammonium hydroxide, and the glucose concentration was maintained at approximately 2% by the addition of a concentrated glucose feed solution. The latter solution comprises (per liter) 400 g glucose, 0.4 g FeCl$_3$·6H$_2$O, 2.6 g MgSO$_4$·7H$_2$O, 20 g sodium citrate, 20 ml trace elements and 20 ml vitamins. The culture was agitated by a rotating impeller at 400–600 rpm. Antifoam was added as needed to prevent significant foaming. After the 4 h incubation period, cells were collected and washed once with TEN buffer (25 mM Tris-HCl, pH 8.0, 10 mM EDTA, 150 mM NaCl). Cells were collected again by centrifugation at 4,000 rpm for 20 min and the pellets were stored at −20° C.

B. Gene Expression and Analysis

Induction of hirudin gene expression was achieved by addition of Mitomycin C to a final concentration of 1 mg/liter or by a shift in temperature from 30° C. to 42° C. for 15-30 min followed by a decrease to 37° C., for the ts strain. After a total induction time of approximately 4 hours [final optical density at 650 nm was approximately 10-12 (laboratory scale culture) or 40-50 (high density culture)], the culture was cooled and the cells were collected by centrifugation or filtration.

Expression of protein synthesis for each of the recombinant proteins of interest following induction was followed by polyacrylamide gel electrophoresis (PAGE) Samples were generally taken from the culture prior to, and 4 h after, the addition of Mitomycin C (hours 0 and 4, respectively). The volume of samples was adjusted for the optical density of the culture such that equal number of cells are taken at a given sampling time. Cells were collected by centrifugation at 6,000 rpm for 5 min and the pellets were freezed and thawed at least once before they were resuspended in 250 ul of sample buffer. The sample buffer consists of 1% SDS, 20% glycerol, 40 mM Tris-HCl, pH 6.8, 0.05% BPB and 0.14M 2-mercaptoethanol for the standard polyacrylamide gel and 2.5% SDS, 10 mM DTT, 10 mM Tris-HCl, pH 8.0, and 0.01% BPB for the Phast gel system (Pharmacia). Samples analyzed by the Phast system were further diluted 40×. Samples were boiled for 5 min before they were loaded on an 8–25% Pharmacia gradient gel or a 15% polyacrylamide-SDS gel. The Phast gel was run and silver-stained according to the procedures and programs provided by the manufacturer. The polyacrylamide-SDS gel was electrophoresed at 30 mAmp for 6 h and stained overnight in a Coomassie blue dye mixture (0.05% Coomassie blue, 25% isopropanol, and 10% acetic acid) and destained in a 25% isopropanol and 10% acetic acid solution. When necessary, gels were quantitated by analysis of photographic negatives of the gel using a laser densitometer with an electronic integrater.

C. Cell Lysis

Cells were resuspended in a buffer consisting of 50 mM Tris, 0.2M NaCl, 5 mM EDTA, pH 8.5, (50–100 ml of buffer per liter of original culture) and lysed using a Stansted Cell Disrupter at a temperature of 5°–10° C., an operating pressure of 11–12,000 psi, and a flow rate of 150-200 ml per min. Insoluble material (containing greater than 85% of the total CTAP-III/hirudin fusion protein) was collected by centrifugation or filtration. The supernatant solution was discarded.

D. Reduction

Insoluble material containing the CTAP-III/hirudin fusion protein was solubilized in 6M guanidine hydrochloride (GnHCl), 50 mM Tris base, 1 mM EDTA, (50 ml per liter of cell culture) and adjusted to a pH between 8.5 and 9.0. Reducing agent (dithiothreitol or beta-mercaptoethanol) was added to a final concentration of 0.1M and the solution was incubated at 37° C. for 1 to 3 hours. The solution was acidified to pH 3–4 and dialyzed against 20–100 volumes of 0.1N acetic acid for 6 to 12 hours with 2 changes. Any resulting precipitate was removed by centrifugation or filtration and discarded. The supernatant was lyophilized.

E. Cyanogen Bromide Cleavage

The crude protein mixture was dissolved in 70% formic acid (approximately 50 ml per liter of cell culture), purged with argon gas, and stirred slowly at room temperature for about 20 min or until most of the material was dissolved. Sodium thiosulfate (approximately 65 mg per liter of culture) was added and stirred for an additional 40 min. Finally, CNBr was added to a final concentration between 0.1 and 0.4M, and the reaction mixture was incubated for 6 to 20 h. Alternatively, the CNBr reaction is carried out using 0.2N HCl and 6M GnHCl as the reaction solvent. The progress of the reaction was followed by analytical HPLC analysis (as described below) of pilot scale reactions. The reaction typically proceeded to greater than 90% completion, at which time the solution was diluted 3- to 5-fold with deionized/distilled water, dialyzed and lyophilized.

Figure 11:
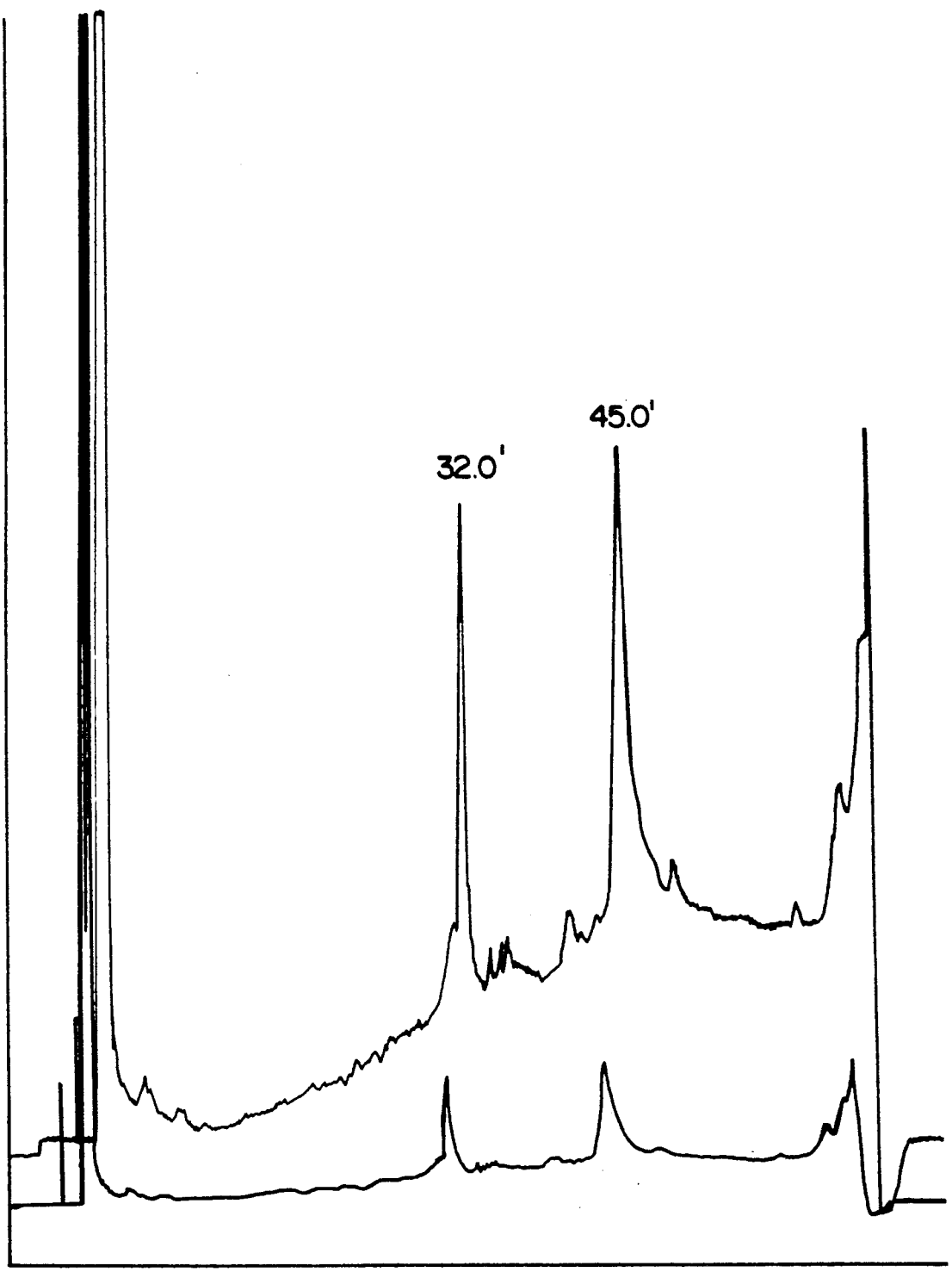
FIG. 11 is a diagram illustrating the quantitation of hirudin expression by separation of hirudin and CTAP-III using reverse phase HPLC following cyanogen bromide cleavage

As shown in FIG. 11, quantitation of hirudin expression by cleavage and separation of hirudin and CTAP-III was determined using RP-HPLC. The yield of hirudin was calculated from the analysis of the dialyzed CNBr reaction mixture both before and after reduction, by analytical HPLC using purified hirudin standards whose concentrations were calibrated by amino acid composition analysis and specific activity measurements.

Reverse phase HPLC analysis was typically performed on 10 ul of the hirudin solution and on 6 ul of hirudin standard (approximately 10 ug each). Samples were adjusted to 15% acetonitrile, 0.065% trifluoroacetic acid (v/v) (TFA) and injected in volumes of 0.1 ml (untreated samples) or 1.0 ml (reduced samples) onto a Vydac C-4 column. Elution was performed using 0.065% TFA with ascending linear gradients of 15 to 30% acetonitrile at a rate of 0.5% acetonitrile per minute. Oxidized and reduced hirudin HV-1 elute at characteristic positions identical with purified hirudin HV-1 having specific activity values greater than 10 antithrombin units per ug.

Hirudin samples were reduced by incubation at 37° C. in 0.1M dithiothreitol, 0.2M Tris base, pH 9, for 45 min prior to acidification and dilution in acetonitrile/TFA and injection onto the HPLC column. The concentration of hirudin in the standard was determined by quantitative composition analysis of an acid hydrolyzate on a Beckman 6300 amino acid analyzer (using an internal standard of known concentration). Calculation of the amount of hirudin in a sample (for example, a CNBr cleavage reaction) is by comparison of the integration of the sample peak and the hirudin standard for both reduced and nonreduced samples. Peak integrations were confirmed in duplicate runs. From this analysis, the yield of hirudin after the CNBr cleavage step was consistently 50-70 mg per liter of original culture grown under low density conditions (final optical density of the culture at 650 nm was 10-12).

F. Anion Exchange Chromatography (AEC)

Protein was dissolved in water at a concentration of 5-25 mg/ml and the pH of the solution was adjusted to 5.5 by the addition of histidine hydrochloride. A column of Q Sepharose (Pharmacia) was equilibrated with 50 mM histidine buffer, pH 5.5. Approximately 5 mg of hirudin was charged onto the column per ml of resin. CTAP-III did not bind to the column under these conditions and eluted in the flow-through. The column was washed with buffer until no further UV absorbing material was detected. The column was then eluted with a 0 to 0.5M gradient of NaCl in histidine buffer. The hirudin eluted between 0.12 and 0.16M NaCl. The elution profile was characterized by a single major peak which had chromatographic properties and thrombin inhibition properties identical with purified recombinant hirudin (HV-1) Hirudin containing fractions were pooled, dialyzed against water and lyophilized. Hirudin preparations at this state were typically greater than 90% pure as determined by HPLC.

G. Protein Refolding

Hirudin was dissolved in 6M GnHCl at a concentration of approximately 100 mg/ml. Beta-mercaptoethanol was added to a final concentration of 0.1 to 0.15M, and the solution was adjusted to a pH of 8.2 with 50 mM Tris base, or to a pH of 10 with 50 mM sodium bicarbonate, 1 mM EDTA. After approximately 1 to 2 h of incubation at room temperature, the solution was diluted 5 to 10 fold with 6M GnHCl in 50 mM buffer, 1 mM EDTA, and then dialyzed over a period of approximately 6 to 18 h against 10 volumes of 50 mM buffer (without GnHCl) during which time refolding to the native conformation occurs. Alternatively, a 2:1 mixture of oxidized and reduced glutathione can be used in the refolding reaction in place of mercaptoethanol. Finally the solution was dialyzed against water.

H. Final Chromatography

Optional chromatography steps may be employed at this point to achieve further purity of the hirudin protein. A second anion exchange chromatography, or hydrophobic interaction chromatography (HIC) or reverse phase chromatography step, for example, will provide a hirudin composition of greater than 95% purity.

HIC was used to purify a sample of recombinant hirudin directly expressed as a nonfused protein in the pNP6ΔRI-CRM/HIR vector. In this example, hirudin was prepared from lysed cells and partially purified by titrating the crude extract with hydrochloric acid to pH 3.8 and discarding the insoluble material. The pH of the supernatant solution was adjusted to neutral pH with sodium hydroxide, diluted to give an ionic strength of approximately 0.1 or less, and charged on a Zeta Prep QAE 60 ion exchange cartridge. The cartridge was washed with 0.1M NaCl in 20 mM bis-Tris buffer pH 6.0 until no further UV absorbing material eluted. Hirudin was eluted from the column using buffer containing 0.4M NaCl. The resulting hirudin was approximately 50% pure as determined by analytical RP-HPLC.

Figure 12:
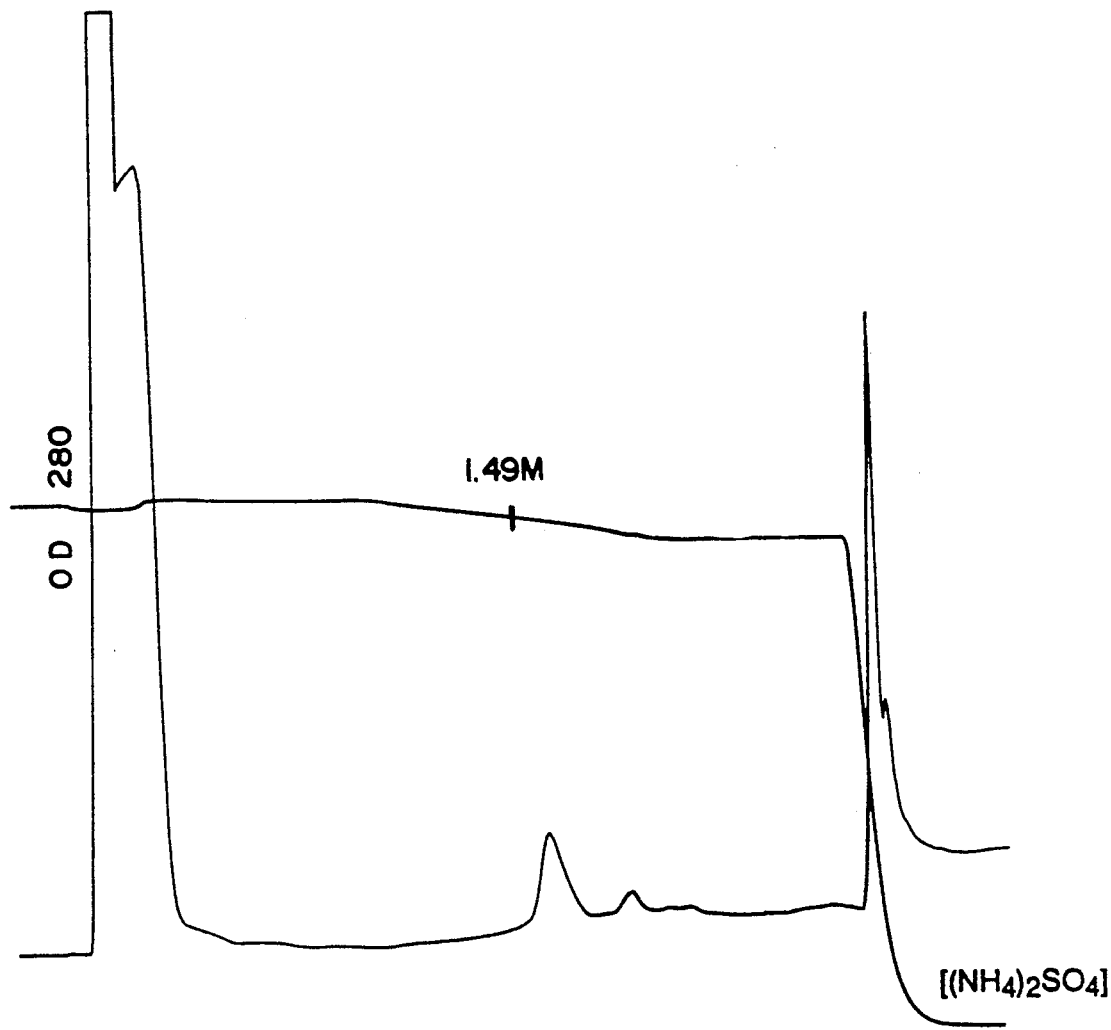
FIG. 12 is a diagram illustrating the purification of hirudin by hydrophobic interaction chromatography (HIC).

The protein was then loaded onto an HIC column, on a semi-preparative scale, containing phenyl Superose (Pharmacia) at an approximate concentration of 0.1 mg hirudin/ml and eluted over a linear gradient of ammonium sulfate from 1.7 to 1.2M in 20 mM bis-Tris, pH 6.0, at a flow rate of 0.5 ml/min. FIG. 12 illustrates the purity of the hirudin recovered from this procedure.

Figure 13:
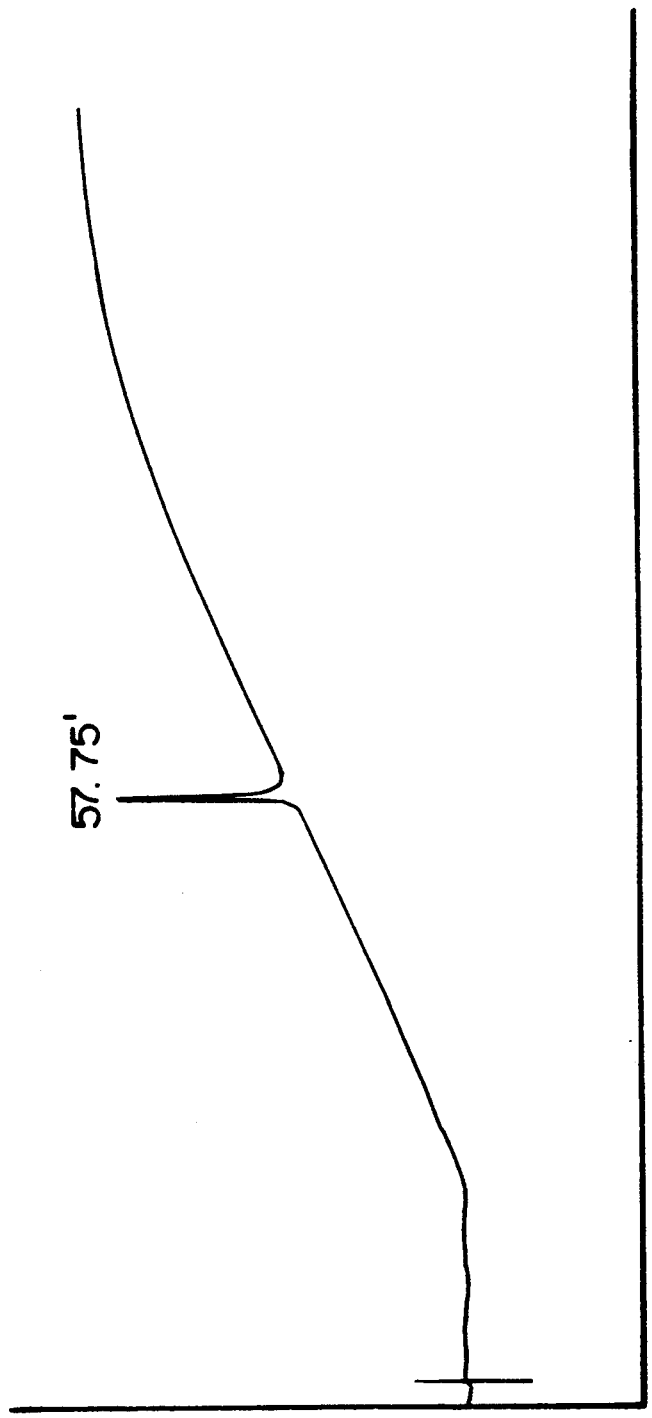
FIG. 13 is a diagram illustrating the purity of hirudin after the final purification step as evaluated by analytical reverse phase HPLC.

The influence of the slope of the salt gradient on the separation was determined by varying the slope from 4.25 to 17 mM ammonium sulfate/min on three successive chromatographic runs. Baseline resolution was observed on all three runs; resolution (defined as the ratio of the distance between peak maxima and the average base width of two peaks) was 2.25 at a gradient of 4.25 mM NaCl/min, 1.68 at 8.5 mM NaCl/min, and 1.48 at 17 mM NaCl/min. (A resolution of 1.5 or greater is baseline resolution.) Recovery determined for the 8.5 mM ammonium sulfate/min gradient was 65% at a loading of 0.133 mg hirudin per ml resin. Under these conditions, hirudin eluted at 1.49M ammonium sulfate; it eluted at a slightly higher salt concentration when using the shallower gradient, and at slightly lower salt under the steeper gradient condition. The purity of eluted hirudin shown in FIG. 13 was greater than 95% as determined by analytical RP-HPLC.

From these results, it would be understood that HIC is an exceedingly useful procedure to obtain hirudin of substantial purity.

Another purification procedure employs gel filtration chromatography following anion exchange chromatography. Hirudin is purified by fast protein liquid chromatography (FPLC) using Superose-12 (Pharmacia). The elution buffer is typically 50 mM sodium phosphate, 0.5M NaCl, 0.1 mM EDTA, pH 7.0, at a flow rate of 0.25-1.5 ml/min. The resulting hirudin is greater than 95% pure.

EXAMPLE 7

Construction of Expression Vectors Containing the Laminin $B_1$-40 Peptide Gene

A. Design and Synthesis of Laminin Gene Fragments

The 6 fragments forming the laminin $B_1$-40 gene, set forth below, were synthesized and gel purified as previously described. Fragments 2, 3, 5 and 6 were kinased and fragments 1 and 4 were not kinased, to prevent the 3' ends from ligating together to form dimers. The 6 fragments were ligated together under the following conditions: 33.3 pmoles oligomers (1 and 4 unkinased; 2, 3, 5 and 6 kinased) were added to 30 mM Tris HCl (pH 7.8), 10 mM $MgCl_2$, and 6 mM DTT, and heated to 90° C. After cooling to room temperature, 1 mM ATP, and 200 cohesive-end-units (NEB) of T4 ligase (1 cohesive end unit=0.015 Weiss units) were added to a volume of 50 ul and the reaction incubated overnight at 16° C. The reaction was subsequently heated for 15 min at 70° C. to inactivate the ligase. The reaction mixture was digested with EcoRI restriction enzyme to separate any 5'-5' dimers. The EcoRI-cut ligation mixture was run on a 2% SeaPlaque® agarose gel and the 143 bp piece was isolated for ligation into the vector. The EcoRI fragment had the following DNA sequence:

in the vector pBR-CRM/CTAP(Leu$_{21}$) was removed by double digestion with XbaI and EcoRI and the vector fragment DNA was purified by SeaPlaque® gel electrophoresis.

To this isolated fragment was added a synthetic 71 bp XbaI-EcoRI linker fragment containing a new CTAP-

```
5'-AATTCGTATG CCGTGCCCGG ATGGTCCGGA CTCCGGCCGT CAGTTCGCTC
  3'-GCATAC GGCACGGGCC TACCAGGCCT GAGGCCGGCA GTCAAGCGAG

GTTCTTGCTA CCAGGACCCG GTTACCCTGC AGCTGGCTTC TGTTTGCGAT
CAAGAACGAT GGTCCTGGGC CAATGGGACG TCGACCGAAG ACAAACGCTA

CCAGGCTACA TCGGTTCTCG TTGCGACGAC TAATGACTGC
GGTCCGATGT AGCCAAGAGC AACGCTGCTG ATTACTGACG

AGAAGCTTC-3'
TCTTCGAAGT TAA-5'
```

B. Construction of pBR-CRM/Col(150)/LamB$_1$-40

The process to construct the colicin(150)/laminin B$_1$-40 gene fusion was accomplished in two steps. A III 3'-end without any translational stop codons. The synthetic linker was synthesized, purified, kinased and ligated as previously described and is shown below:

```
5'-CTAGACCCGG ACGCTCCACG TATCAAGAAG ATCGTTCAGA AAAAACTGGC
   3'-TGGGCC TGCGAGGTGC ATAGTTCTTC TAGCAAGTCT TTTTTGACCG

TGGTGACGAA TCTGCTGACA G-3'
ACCACTGCTT AGACGCTTGT CTTAA-5'
``` first vector was prepared by inserting the 143 bp laminin gene fragment (prepared as described above) into EcoRI-digested pBR-CRM/CTAP(Leu$_{21}$) The SacII-EcoRI fragment containing the gene encoding CTAP-III(Leu$_{21}$) was removed from this vector by double digestion and subsequent agarose gel purification of the remaining vector DNA containing the laminin gene fragment. The colicin(150) gene fragment was prepared similarly by SacII-EcoRI digestion of pNP6ΔRI-CRM/Col(150)/PF4. The pBR-CRM/LamB$_1$-40 vector and the colicin 150 gene fragment were then ligated to produce pBR-CRM/Col(150)/LamB$_1$-40. Clones were screened by restriction analyses of purified plasmid DNA prepared as described in Example 3, and demonstrated several likely candidates, but protein gel analysis of induced cultures of these clones showed little, if any, induction of any protein of the expected size (~21,000 daltons) of the Col(150)/LamB$_1$-40 fusion protein. Partial sequencing of these clones demonstrated the presence of the laminin gene sequence in the The two fragments were then ligated together under conditions described previously using 1.0 pmole of linker and 0.1 pmole of vector in a 172 ul reaction volume. 100 ul of frozen competent E. coli 294 cells were transformed with 1-10 ng of the ligation mixture to construct an intermediate cloning vector. Resulting clones were screened by restriction enzyme analysis as described previously. The DNA of a representative clone was sequenced to confirm the correct DNA sequence. This clone was grown up to produce sufficient amounts for subsequent insertion of the new laminin gene.

A new laminin gene was constructed to (1) put CTAP in phase with laminin for the gene fusion, (2) remove a HindIII site (leaving one HindIII site in the new plasmid to be used as a unique restriction site), and (3) add three new unique restriction sites (StuI, SmaI and SalI) for future laminin gene cassette mutagenesis. The oligonucleotides and the ligation strategy is provided below:

```
5'-AATTCGTAT GCCGTGCCCG GATGGTCCGG ACTCCGGCCG TCAGTTCGCT
   3'-GCATA CGGCACGGGC CTACCAGGCC TGAGGCCGGC AGTCAAGCGA

CGTTCTTGCT ACCAGGACCC GGTTACCCTG CAGCTGGCTA GCGTTTGCGA
GCAAGAACGA TGGTCCTGGG CCAATGGGAC GTCGACCGAT CGCAAACGCT

CCCGGGCTAC ATCGGTTCTC GTTGCGACGA CTAATGAGTC
GGGCCCGATG TAGCCAAGAG CAACGCTGCT GATTACTCAG

GACAGGCCTC-3'
CTGTCCGGAG TTAA-5'
``` correct translational reading frame with the 5' end of the colicin gene sequence.

C. Construction of pBR-CRM/CTAP(Leu$_{21}$)/LamB$_1$-40

Cloning of the CTAP/LamB$_1$-40 fusion was accomplished as follows. A portion of the 3'-end of CTAP-III As in the colicin-laminin gene construction, the 5' EcoRI site was active, while the 3' EcoRI site was mutated (GAATTC→CAATTC) to leave a unique EcoRI site.

This new gene fragment was inserted as follows into the intermediate vector construction at the unique EcoRI site, thereby introducing the laminin coding sequence in phase with the end of the CTAP coding sequence.

The intermediate plasmid was digested with EcoRI, treated with calf intestinal phosphatase (CAP) to remove 5'-phosphate groups to prevent religation of the vector onto itself, and purified by agarose gel electrophoresis. The new laminin gene was constructed, purified, kinased, and ligated as described previously. These two pieces were then ligated together and the ligation mixture was used to transform competent *E. coli* 294 cells. Six clones were picked and analyzed by induction with Mitomycin C to determine if a protein of the correct size (135 amino acids, ~15,000 daltons) was produced. Two of the six clones specifically induced a protein of this size.

These clones were then screened for the correct orientation of the laminin gene insert by double digestion with EcoRI and XhoI. The correct orientation gave two fragments of 308 bp and 3940 bp. The incorrect orientation gave two fragments of 457 bp and 3791 bp. Two of the six clones had the correct orientation. The correct structure of the gene was confirmed by double-stranded DNA sequencing.

EXAMPLE 8

Expression, Purification and Assays for the Laminin $B_1$-40 Peptide

Expression of the CTAP/LamB$_1$-40 peptide fusion in shake flasks or fermenter cultures was performed as previously described.

Figure 7A:
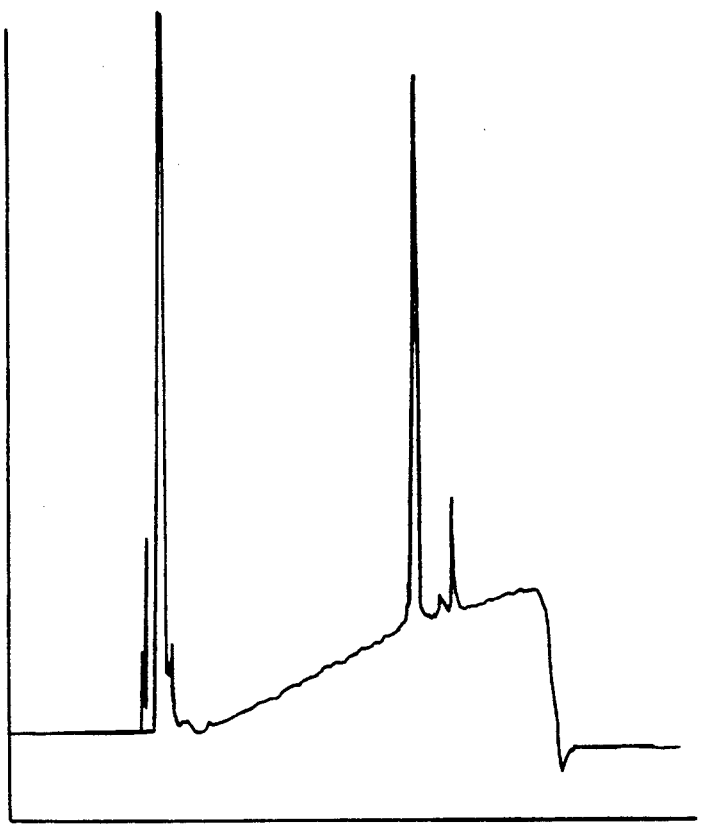
FIG. 7A and FIG. 7B are diagrams showing the reverse phase HPLC purification profile of the CTAP-III/LamB$_1$-40 protein(s) before (A) and after (B) cyanogen bromide cleavage.

The purification of the laminin B$_1$-40 peptide is described below. Cells were harvested as described for hirudin and lysed by sonication (2×) in one-tenth the original culture volume of 25 mM Tris-HCl (pH 8.0), 1 mM EDTA, and 50 mM glucose (TEG). The insoluble fusion peptide was collected by centrifugation for 20 min at 15,000 rpm in an SS-34 rotor at 4° C. The pellets were resuspended in one-tenth the original culture volume of 7M urea, 25 mM Tris-HCl (pH 8.0), 1 mm EDTA (or 6M GnHCl, 25 mM Tris-HCl, pH 8.0, 1 mM EDTA) and sonicated 6× on ice (#8 setting, large tip, Branson 350 watt sonicator) for 2 min with a 5 min rest. (Some preparations were made using 1 mM PMSF to inhibit proteases during the cell lysis and solubilization steps.) The suspension was centrifuged as above for 30 min at 5,000 rpm in an SS-34 rotor. The supernatant solution (~500 ml) was dialyzed for 1-3 days versus 50 liters of 10 mM acetic acid at 4° C. until a heavy precipitate formed in the dialysis bags (3,500 molecular weight cut-off). The suspension was centrifuged (15 min, 15,000 rpm, SS-34 rotor, 4° C.). The pellet and supernatant were analyzed for the presence of the ~15,000 dalton band by SDS-polyacrylamide gel electrophoresis. Normally, the vast majority (>90%) of the fusion protein was found in the pellet. If this was not the case, the total suspension was lyophylized to dryness. FIG. 7A shows the HPLC purification profile of the CTAP-laminin fusion protein prior to cyanogen bromide cleavage.

Cyanogen bromide cleavage of the CTAP/laminin fusion was performed as described in Example 6E. The dialyzed and lyophilized CNBr reaction products were dissolved in approximately 200 ml 6M GnHCl and titrated to pH 9-10 with 2M Tris base. DTT was added to 0.1M and the reaction mixture was incubated at 37° C. for 1 h to reduce all protein. The pH of the reaction was adjusted to 2.5-3.5 by addition of approximately one-fiftieth volume of 88% formic acid, to keep the cysteines reduced. This material was made 15% in acetonitrile for HPLC analysis. Any precipitate that formed was removed by centrifugation and filtration.

Figure 7B:
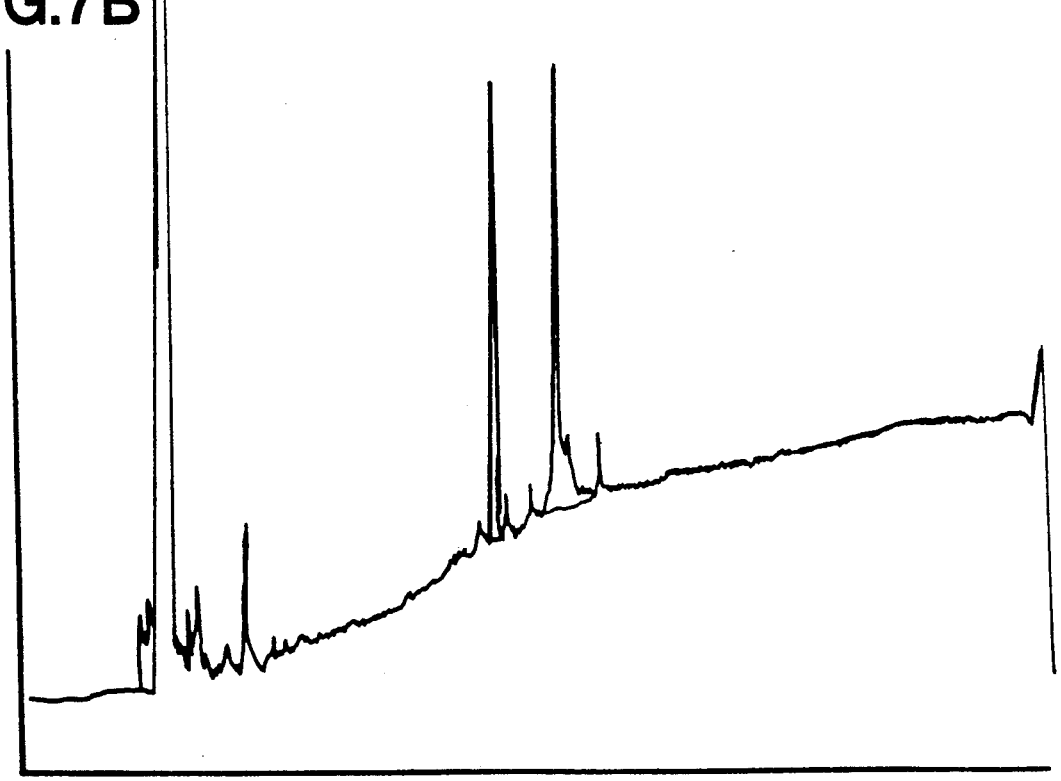

Analytical HPLC was performed on a Water's 680 system (680 controller, 2-510 pumps, 490E detector) using a 15 to 40% gradient in solvent B, at 0.5%/min, 2 ml/min. where A solvent is 0.065% (v/v) TFA (Pierce Sequanol ampoules) in water (Burdick and Jackson) and solvent B is 0.065% (v/v) TFA in acetonitrile (CH$_3$CN, Burdick and Jackson, UV grade) using a Vydac 214TP54 column (C4, 300 Å pore size, 5 u beads, 4.6 mm×250 mm). The monitoring wavelength was 215 nm. The results (FIG. 7B) showed two major peaks, the first of which was demonstrated to be the laminin B$_1$-40 peptide (by amino acid sequencing and composition analysis) and the second was identified to be the CTAP-III protein, plus the three linking amino acids (Arg-Ile-Arg), by its retention time compared to CTAP-III.

Preparative HPLC was performed on a Separations Technology 800B instrument outfitted with a 75 mm×250 mm A/E (annular expansion) column packed with approximately 1000 ml of Vydac 214TPB1520 (C4, 300 Å pore size, 15-20 u bead size). Separation was achieved by loading the sample at 15% solvent B, running a short 15-20% B gradient and eluting the laminin B -40 and CTAP-III(Arg-Ile-Arg) using an 80 min 20-40% B gradient (320 ml/min) monitoring at 215 nm. As was the case on the analytical HPLC separation, the same two major peaks were observed. Appropriate fractions were identified by analytical RP-HPLC, pooled and lyophylized to dryness.

The laminin B$_1$-40 peptide was refolded as described for hirudin in Example 6G.

EXAMPLE 9

Cell Adhesion Assay

The laminin B$_1$-40 peptide, along with the previously described YIGSR and CDPGYIGSR peptides, were dissolved in phosphate-buffered saline (PBS) and were coated onto Falcon #3915 polystyrene 96-well plates at 37° C. for 60 min. The peptide solutions were removed, and the wells were washed twice with PBS. Non-specific cell binding was prevented by adding 200 ul 0.1% bovine serum albumin (BSA) (Sigma #4965) in PBS to the wells and incubating for 60 min at 37° C. The BSA was removed by washing twice with PBS. B16/F10 cells (murine melanoma) in log phase growth were harvested after 2 min exposure to 0.05% trypsin/0.1% EDTA in PBS, suspended in growth medium (DMEM +10% FBS), centrifuged, and resuspended in binding medium (DMEM+20 mM HEPES+0.1% BSA). 100 ul of cells (3-4×10$^4$ cells) were added to each well and incubated for 60 min at 37° C. Non-adherent cells were removed by rapid rotation of the plate, addition of PBS, aspiration of all but 50 ul of the contents of the wells; the washing procedure was repeated two more times. After the final wash, the entire solution was slowly aspirated, and the cells were fixed by the addition of 100 ul methanol for 15 min. The methanol was removed and the cells were air-dried before staining for 5 min with 100 ul 0.1% crystal violet solution. The stain was removed and the wells were washed with 200 ul H$_2$O and air dried. The cells were solubilized by adding 100 ul of 2% deoxycholic acid and heating gently in a microwave oven. The optical density of the solutions was read on a Molecular Devices Corporation plate reader at a wavelength between 590 nm and 405 nm. Extrapolation of optical density to number of cells bound was done by comparison of readings to a standard curve obtained by incubating various numbers of cells in microtiter plate wells for 5 h (to allow firm attachment but no significant dividing), and washing and staining as described above.

Table 2 shows that the recombinant laminin peptide (LamB$_1$-40) binds metastatic tumor cells more effectively in this assay than the previously reported small synthetic peptides YIGSR or CDPGYIGSR. P$_1$ is a protease digestion product of mouse laminin used as a positive control.

TABLE 2

| ug/ml Peptide* | P$_1$ | Reduced LamB$_1$-40 | Refolded LamB$_1$-40 | YIGSR | CDPGYIGSR |
|---|---|---|---|---|---|
| 0.00063 | 0.1 | | | | |
| 0.002 | 1.95 | | | | |
| 0.0063 | 2.3 | | | | |
| 0.02 | 2.3 | 0.85 | | 0.15 | 0.2 |
| 0.063 | | 0.95 | 0.025 | | |
| 0.20 | | 1.35 | 0.6 | 0.1 | 0.3 |
| 0.63 | | 2.20 | 0.5 | | |
| 2.00 | | 1.85 | 0.45 | 0.1 | 0.45 |

*Concentration of the peptide used to coat the wells of the microtiter plate.

EXAMPLE 10

Construction of pBR-CRM/CTAP(Met$_{21}$)/PF4

The cloning of a hybrid gene coding for a CTAP/PF4 fusion was accomplished in three parts: The substituted Leu$_{21}$ of CTAP-III was changed back to the native methionine to construct the vector designated pNP6ΔRI/CTAP(Met$_{21}$). The 303 bp XhoI-EcoRI fragment containing the full-length native CTAP-III gene was excised from this vector and used to replace the same CTAP region in the plasmid pBR-CRM/CTAP(Leu$_{21}$)/LamB$_1$-40 (described previously in Example 7C) to create pBR-CRM/CTAP(Met$_{21}$)-/LamB$_1$-40.

Lastly, the PF4 gene was removed from plasmid pNP6ΔRI/Col(150)/PF4 as a 239 bp EcoRI fragment (the identical sequence is provided in FIG. 3) and ligated to the vector fragment described above to construct a vector designated pBR-CRM/CTAP(-Met$_{21}$)/PF4. The laminin gene present 3' to the CTAP PF4 gene fusion is not expressed due to the presence of stop codons at the 3' end of the PF4 gene.

This vector was used to transform *E. coli*, ampicillin-resistant transformants are selected and isolated clones analyzed by restriction digest for identification of the correct gene orientation. Positive clones may then be induced for expression of the CTAP-PF4 fusion protein.

Modifications of the above described modes for carrying out the invention that are obvious to those of skill in the art of molecular biology, protein chemistry, cell biology, or related fields are intended to be within the scope of the following claims.

We claim:

1. In a method for purifying an heterologous polypeptide from a fusion polypeptide produced in a recombinant bacterial microorganism which method comprises the steps of expressing a fusion polypeptide composed of a connective tissue activating-peptide III polypeptide and the heterologous polypeptide separated by an intervening selectable cleavage site, separating the fusion polypeptide by cleaving at the selectable cleavage site, and subsequently recovering the heterologous polypeptide, said improvement employing a connective tissue activating-peptide III polypeptide having a selectable internal cleavage site whereby said separation step cleaves the fusion polypeptide and internally cleaves the connective tissue activating-peptide III polypeptide to produce connective tissue activating-peptide III peptides, each peptide having an isoelectric point difference of a minimum of approximately 1.5 pH units between the heterologous polypeptide and the connective tissue activating-peptide III peptide.

2. The method of claim 1, wherein the pI value of the heterologous polypeptide is between about 6.5 and about 8.5, and the internal cleavage site of connective tissue activating-peptide III separates connective tissue activating-peptide III into two peptides, the pI value of the first peptide of about 4.2 and the pI value of the second peptide of about 9.3.

3. The method of claim 1, wherein the selectable cleavage sites are methionine residues.

4. The method of claim 1, wherein ion exchange chromatography is employed in the recovery step.

* * * * *

UNITED STATES PATENT AND TRADEMARK OFFICE
CERTIFICATE OF CORRECTION

PATENT NO. : 5,179,196
DATED : 01/12/93
INVENTOR(S) : Paul H. Johnson, Richard C. Winant, Jerome B. Lazar It is certified that error appears in the above-identified patent and that said Letters Patent is hereby corrected as shown below:

On the title page, item (75) delete "Ping Sze;"

Signed and Sealed this

First Day of February, 1994

*Attest:*

BRUCE LEHMAN

*Attesting Officer*  Commissioner of Patents and Trademarks